(12) United States Patent
Hamm et al.

(10) Patent No.: US 6,559,128 B1
(45) Date of Patent: May 6, 2003

(54) INHIBITORS OF G PROTEIN-MEDIATED SIGNALING, METHODS OF MAKING THEM, AND USES THEREOF

(75) Inventors: Heidi E. Hamm, Chicago, IL (US); Annette Gilchrist, Lombard, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/489,156

(22) Filed: Jan. 21, 2000

(51) Int. Cl.⁷ .......................... C07H 17/00; C07K 14/00
(52) U.S. Cl. ..................... 514/44; 514/2; 514/13; 514/14; 536/23.5; 536/23.1; 530/300; 530/326; 530/327
(58) Field of Search ............... 536/23.1, 23.4, 536/23.5; 435/6, 7.1, 320.1; 514/2, 13, 14, 44; 530/300

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 5,034,506 A | 7/1991 | Summerton et al. | 528/391 |

FOREIGN PATENT DOCUMENTS

WO   WO99/18211   *   4/1999

OTHER PUBLICATIONS

PNAS, vol. 85, pp. 5384–5388, 1988, Matsuoka et al.*
Conklin et al., 1993, Nature 363: 274–276.
Conklin et al., 1996, Mol. Pharmacol. 50: 885–890.
Farfel et al., 1999, New Engl. J. Med. 340: 1012–20.
Flanagan et al., 1997, Rev. Reprod. 2:113–120.
Ford et al., 1998, Science 280:1271–1273.
Garcia et al., 1995, EMBO 14: 4460–9.
Gilchrist et al., 1998, J. Biol. Chem 273: 14912–14919.
Gilchrist et al., 1999, J. Biol. Chem. 274: 6601–6606.
Gromoll et al., 1996, Mol. Cell Endocrinol. 125:177–82.
Hamm et al., 1988, Science 241:832–835.
Hamm et al., 1996, Curr. Opin. Cell. Biol. 8: 189–196.
Hamm, 1998, Science 273: 669–672.
Holler et al., 1999, Cell. Mol. Life Sci. 55: 257–70.
Inanobe et al., 1999, J. Physiol. (Lond) 521 :19–30.
Nielsen et al., 1991, Science 254: 1497.
Osawa et al., 1995, J. Biol. Chem. 270: 31052–8.
Rasenick et al., 1994, J. Biol. Chem. 269: 21519–21525.
Sullivan et al., 1987, Nature 330: 758–760.
West et al., 1985, J. Biol. Chem. 260: 14428–30.

* cited by examiner

*Primary Examiner*—Karen Cochrane Carlson
(74) *Attorney, Agent, or Firm*—Morgan, Lewis & Bockius LLP

(57) ABSTRACT

The invention provides compositions and methods useful for blocking G protein-mediated signaling events. Compositions provided by the invention relate to carboxy terminal Gα peptides, and minigenes which encode such peptides. The invention provides methods of making the minigenes, and methods of using either of the minigenes and the Gα carboxy terminal peptides encoded thereby, to block G protein-mediated signaling events. The invention also provides methods of using either of the minigenes and the Gα carboxy terminal peptides encoded thereby for the identification of unknown interactions between G proteins and G protein coupled receptors, and for the treatment of pathological disorders associated with G protein-mediated signaling events.

8 Claims, 17 Drawing Sheets

| NUCLEOTIDE SEQUENCE | SEQ ID NO. |
|---|---|
| 5' gatccgccgccacc atg gga atc aag gaa aac ctg aag gaa gac tgc ggc ctc ttc tgaa 3' | 1 |
| 5' gatccgccgccacc atg gga atc aag aac aac ctg aag gac tgc ggc ctc ttc tgaa 3' | 2 |
| 5' gatccgccgccacc atg gga aac ggc atc aag tgc ctc aac gac aag ctg tgaa 3' | 3 |
| 5' gatccgccgccacc atg gga att aaa aac tta aag gaa tgt gga ctt tat tgaa 3' | 4 |
| 5' gatccgccgccacc atg gga atc gcc aaa aac ctg cgg ggc tgt gga ctc tac tgaa 3' | 5 |
| 5' gatccgccgccacc atg gga att gcc aac aac ctc cag cgg ggc tgc ttg tac tgaa 3' | 6 |
| 5' gatccgccgccacc atg gga ata cag aac aat ctc aag tac att ggc ctt tgc tgaa 3' | 7 |
| 5' gatccgccgccacc atg gga ctg cag ctg aac ctg aag gag tac aat ctg gtc tgaa 3' | 8 |
| 5' gatccgccgccacc atg gga ctc cag ttg aac ctg aag gag tac aat gca gtc tgaa 3' | 9 |
| 5' gatccgccgccacc atg gga cag cgg atg cac ctc aag cag tat gag ctc ttg tgaa 3' | 10 |
| 5' gatccgccgccacc atg gga cta cag cta aac cta agg gaa ttc aac ctt gtc tgaa 3' | 11 |
| 5' gatccgccgccacc atg gga ctc gcc cgg tac ctg gac gag att aat ctg ctg tgaa 3' | 12 |
| 5' gatccgccgccacc atg gga ctg cag gag aac ctg aag gac atc atg ctg cag tgaa 3' | 13 |
| 5' gatccgccgccacc atg gga cag cgc atg cac ctt cgt cag tac gag ctg ctc tgaa 3' | 14 |

FIG. 2A

| NAME | AMINO ACID SEQUENCE | | | | | | | | | | SEQ ID NO. |
|---|---|---|---|---|---|---|---|---|---|---|---|
| Gα$_t$ | M | G | I | K | E | N | L | K | D | C | G | L | F | 15 |
| Gα$_{i1/2}$ | M | G | I | K | N | N | L | K | D | C | G | L | F | 16 |
| Gα$_iR$ | M | G | N | G | I | N | C | L | F | N | D | K | L | 17 |
| Gα$_{i3}$ | M | G | I | K | N | N | L | K | E | C | G | L | Y | 18 |
| Gα$_{o2}$ | M | G | I | A | K | N | L | R | G | C | G | L | Y | 19 |
| Gα$_{o1}$ | M | G | I | A | N | N | L | K | G | C | G | L | Y | 20 |
| Gα$_z$ | M | G | I | Q | L | N | L | K | Y | I | G | L | C | 21 |
| Gα$_{11}$ | M | G | L | Q | L | N | L | K | E | Y | N | L | V | 22 |
| Gα$_q$ | M | G | Q | Q | M | H | L | K | E | Y | E | A | V | 23 |
| Gα$_{olf}$ | M | G | L | R | L | N | L | K | Q | F | N | L | L | 24 |
| Gα$_{14}$ | M | G | L | Q | E | Y | L | R | E | H | N | L | V | 25 |
| Gα$_{15/16}$ | M | G | L | A | R | N | L | D | D | I | M | L | L | 26 |
| Gα$_{12}$ | M | G | L | Q | E | N | L | K | Q | L | M | L | Q | 27 |
| Gα$_{13}$ | M | G | L | H | D | H | L | R | Q | Y | M | L | Q | 28 |
| Gα$_s$ | M | G | Q | R | M | N | L | R | Q | Y | E | L | L | 29 |

FIG. 2B

| NAME | NUCLEOTIDE SEQUENCE | SEQ ID NO. |
|---|---|---|
| $G_{i3}$ | att aaa aac aac tta aag gaa tgt gga ctt tat | 30 |
| $G_{o2}$ | atc gcc aaa aac ctg cgg ggc tgt gga ctc tac | 31 |
| $G_z$ | ata cag aac aat ctc aag tac att ggc ctt tgc | 32 |
| $G_{11}$ | ctg cag ctg aac ctg aag gag tac aat ctg gtc | 33 |
| $G_{olf}$ | cag cgg atg cac ctc aag cag tat gag ctc ttg | 34 |
| $G_{14}$ | cta cag cta aac cta agg gaa ttc aac ctt gtc | 35 |
| $G_{15/16}$ | ctc gcc cgg tac ctg gac gag att aat ctg ctg | 36 |
| $G_{12}$ | ctg cag gag aac ctg aag gac atc atg ctg cag | 37 |
| $G_{13}$ | ctg cat gac aac ctc aag cag ctt atg cta cag | 38 |

FIG. 2C

| NAME | AMINO ACID SEQUENCE | | | | | | | | | | SEQ ID NO. |
|---|---|---|---|---|---|---|---|---|---|---|---|
| Gα$_{i3}$ | I | K | N | N | L | K | E | C | G | L | Y | 39 |
| Gα$_{o2}$ | I | A | K | N | L | R | G | C | G | L | Y | 40 |
| Gα$_z$ | I | Q | N | N | L | K | Y | I | G | L | C | 41 |
| Gα$_{11}$ | L | Q | Q | L | N | L | K | Y | N | L | V | 42 |
| Gα$_{olf}$ | Q | R | M | H | L | K | Q | Y | E | L | L | 43 |
| Gα$_{14}$ | L | Q | L | N | L | R | E | F | N | L | V | 44 |
| Gα$_{15/16}$ | L | A | R | Y | L | D | E | I | N | L | L | 45 |
| Gα$_{12}$ | L | Q | E | N | L | K | D | I | M | L | Q | 46 |
| Gα$_{13}$ | L | H | D | N | L | K | Q | L | M | L | Q | 47 |

FIG. 2D

INHIBITORS OF G PROTEIN-MEDIATED SIGNALING, METHODS OF MAKING THEM, AND USES THEREOF

STATEMENT REGARDING FEDERALLY SUPPORTED RESEARCH OR DEVELOPMENT

This research was supported in part by U.S. Government funds (National Institutes of Health, grant numbers HL63341-01 and EI10291), and the U.S. Government may therefore have certain rights in the invention.

BACKGROUND OF THE INVENTION

Many biologically active molecules transduce their signals through heptahelical receptors called G protein coupled receptors (GPCRs), which interact specifically with heterotrimeric guanine nucleotide-binding proteins, called G proteins. The interaction of a G protein with its cognate GPCR results in the initiation of intracellular signaling events which, in turn, lead to a variety of important cellular responses (Hamm et al., 1996, Curr. Opin. Cell. Biol. 8: 189–196; Hamm, 1998, Science 273: 669–672). Stimulation of a GPCR by its appropriate agonist causes conformational changes within the receptor that lead to the interaction of the activated receptor with a specific heterotrimeric G protein. Thus, the GPCR-G protein interaction plays an important role in determining the specificity and temporal characteristics of a variety of cellular responses.

Heterotrimeric G proteins are composed of a single α subunit complexed with the βγ dimer. Molecular cloning has resulted in the identification of 18 distinct α subunits, 5 β subunits, and 12 γ subunits. G proteins are usually divided into four subfamilies $G_i$, $G_s$, $G_q$, and $G_{12}$ based on the sequence similarity of the Gα subunit. Several lines of evidence suggest that the interaction between a given GPCR and its cognate G protein involves multiple sites of contact on both proteins. All three intracellular loops as well as the carboxyl terminal tail of the receptor have been implicated. The GPCR is thought to interact with all three subunits of the G protein. As the receptor-G protein interaction can be disrupted by a number of treatments that block the carboxyl terminus, including pertussis toxin-catalyzed ADP-ribosylation of $G_i$ and binding of monoclonal antibodies, the carboxy terminal region of the Gα subunit has been the most intensely investigated contact site. These studies have shown that the Gα carboxy terminal region is important not only to the interaction, but also plays a critical role in defining receptor specificity (Hamm et al., 1988, Science 241: 832–5; Osawa et al., 1995, J. Biol. Chem. 270: 31052–8; Garcia et al., 1995, EMBO 14: 4460–9; Sullivan et al., 1987, Nature 330: 758–760; Rasenick et al., 1994, J. Biol. Chem. 269: 21519–21525; West et al., 1985, J. Biol. Chem. 260: 14428–30; Conklin et al., 1993, Nature 363: 274–276; Conklin et al., 1996, Mol. Pharmacol. 50: 885–890). Furthermore, it has been shown that peptides corresponding to the carboxy terminal region of a Gα subunit can block GPCR signaling events (Hamm et al., 1988, Science 241: 832–5; Gilchrist et al., 1998, J. Biol. Chem 273: 14912–19).

Because many medically significant biological processes are mediated by G proteins and their downstream effector molecules, the GPCRs with which they interact, have been the focus of intense drug discovery efforts (Holler et al:, 1999, Cell. Mol. Life Sci. 55: 257–70; Farfel et al., 1999, New Engl. J. Med. 340: 1012–20). A number of therapeutic agents targeting GPCRs have been discovered. Traditionally, the agonist binding site on the GPCR is the point of intervention. However, for some GPCR's, classical antagonists have been difficult to identify. Such is the case for proteinase activated receptors (PAR), classical antagonists are ineffective due to the unique mechanism of enzymatic cleavage of the receptor and generation of a tethered ligand. In other cases, intrinsic or constitutive activity of receptors directly leads to pathology. Thus, alternative targets for blocking downstream consequences of GPCR signaling are needed. Agents are needed that can inhibit GPCR by blocking the receptor-G protein interface. The present invention satisfies these needs.

BRIEF SUMMARY OF THE INVENTION

The present invention includes an isolated nucleic acid comprising a minigene, wherein said minigene encodes a modified carboxy terminal Gα peptide, wherein said peptide blocks the site of interaction between a G protein and a G protein coupled receptor in a cell, such as a human cell. In addition, the minigene can further comprise one or more of a promoter, a ribosomal binding site, a translation initiation codon, and a translation termination codon.

In one embodiment, the nucleotide sequence of a minigene of the invention can be one of SEQ ID NOs: 2, 3, 4, 5, 6, 7, 8, 9, 10, 11, 12, 13, and 14.

In another embodiment, a minigene encodes a modified carboxy terminal Gα peptide having one of the following general formulas: MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide which comprises an amino acid sequence of the carboxy terminus of a Gα subunit, and has the property of binding a G protein coupled receptor. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit. For example, the amino acid sequence of a modified carboxy terminal Gα peptide can be one of SEQ ID NOs: 15, 16, 17, 18, 19, 20, 21, 22, 23, 24, 25, 26, 27, 28, and 29.

The present invention also includes a composition comprising a modified carboxy terminal Gα peptide having a general formula selected from the group consisting of MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide which comprises an amino acid sequence of the carboxy terminus of a Gα subunit, and has the property of binding a G protein coupled receptor. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit. For example, the amino acid sequence of a modified carboxy terminal Gα peptide can be one of SEQ ID NOs: 15, 16, 17, 18, 19, 20, 21, 22, 23, 24, 25, 26, 27, 28, and 29.

Additionally, the invention includes a pharmaceutical composition comprising a pharmaceutically acceptable carrier and one of a modified carboxy terminal Gα peptide and a minigene encoding a modified carboxy terminal Gα peptide.

In one aspect, the invention encompasses a method of inhibiting a G protein-mediated signaling event in a cell. This method comprises administering to a cell, preferably a human cell, one of a modified carboxy terminal Gα peptide, and an isolated nucleic acid comprising a minigene which encodes a modified carboxy terminal Gα peptide, whereby following the administration, the carboxy terminal Gα peptide inhibits the G protein mediated signaling event in the cell.

Additionally, the invention includes a method of blocking the site of interaction between a G protein and a G protein coupled receptor in a cell. This method comprises administering to a cell, preferably a human cell, one of a modified carboxy terminal Gα peptide, and an isolated nucleic acid comprising a minigene which encodes a modified carboxy terminal Gα peptide, whereby following the administration, the modified carboxy terminal Gα peptide blocks the site of interaction between the G protein and the G protein coupled receptor in the cell.

Further, the invention includes a method of inhibiting one or more of migration, permeability, and proliferation of a cell. This method comprises administering to a cell, preferably a human cell, one of a modified carboxy terminal Gα peptide, and an isolated nucleic acid comprising a minigene which encodes a modified carboxy terminal Gα peptide, wherein the modified carboxy terminal Gα peptide blocks a G protein-mediated signaling event in a cell, thereby inhibiting one or more of migration, permeability, and proliferation of a cell.

In one embodiment, the preferred cell is a human cell.

In other embodiments, the modified carboxy terminal Gα peptide, either as administered or as expressed from a minigene of the invention, has a general formula. selected from the group consisting of MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide comprising an amino acid sequence of the carboxy terminus of a Gα subunit, and having the property of binding a G protein coupled receptor. In these embodiments, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit. For example, the amino acid sequence of a modified carboxy terminal Gα peptide can be one of SEQ ID NOs: 15, 16, 17, 18, 19, 20, 21, 22, 23, 24, 25, 26, 27, 28, and 29. As an alternative example, the nucleotide sequence of a minigene can be any of SEQ ID NOs: 1, 2, 3, 4, 5, 6, 7, 8, 9, 10, 11, 12, 13, and 14.

The invention encompasses a method of identifying which G protein binds a G protein coupled receptor in a cell. This method comprises administering to the cell an isolated nucleic acid comprising a minigene which encodes a modified carboxy terminal Gα peptide, and assessing the level of occurrence of a signaling event in the cell. According to this method, the signaling event is associated with the G protein coupled receptor, and a measurable reduction in the level of occurrence of the signaling event in the cell compared with the level of occurrence of the same event in a cell to which the isolated nucleic acid is not administered, is an indication that said modified carboxy terminal Gα peptide identifies a G protein that binds said G protein coupled receptor.

The invention additionally includes a method of treating a pathological disorder in a mammal. This method comprises administering to the mammal an amount of either a modified carboxy terminal Gα peptide or an isolated nucleic acid comprising a minigene which encodes a modified carboxy terminal Gα peptide. According to the method, the amount of either the modified carboxy terminal Gα peptide or the isolated nucleic acid is sufficient to inhibit a G protein-mediated signaling event associated with the pathological disorder, and thereby alleviate at least one symptom of the pathological disorder.

In one embodiment, the method of treating a pathological disorder in a mammal includes administering to the mammal a modified carboxy terminal Gα peptide having a general formula selected from the group consisting of MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide which comprises an amino acid sequence of the carboxy terminus of a Gα subunit, and has the property of binding a G protein coupled receptor. In these embodiments, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit. For example, the amino acid sequence of a modified carboxy terminal Gα peptide can be one of SEQ ID NOs: 15, 16, 17, 18, 19, 20, 21, 22, 23, 24, 25, 26, 27, 28, and 29. As an alternative example, the nucleotide sequence of a minigene can be any of SEQ ID NOs: 1, 2, 3, 4, 5, 6, 7, 8, 9, 10, 11, 12, 13, and 14.

In multiple embodiments, the method of the invention is useful for treating a pathological disorder selected from the group consisting of stroke, myocardial infarction, restenosis, atherosclerosis, hypotension, hypertension, angina pectoris, acute heart failure, cardiomyocyte apoptosis, cancers, bacterial infections, fungal infections, protozoan infections, viral infections, septic shock, pain, chronic allergic disorders, asthma, inflammatory bowel disease, osteoporosis, rheumatoid arthritis, Grave's disease, postoperative ileus, diabetes, adult respiratory distress syndrome, myasthenia gravis, cardiovascular disease, congestive heart failure, Chagas disease, disorders associated with solid organ transplant, vascular sclerosis, chronic rejection, chronic obstructive pulmonary disease, urinary retention, testotoxicosis, infertility, ulcers, obesity, benign prostatic hypertrophy, anxiety, epilepsy, schizophrenia, manic depression, Parkinson's disease, Alzheimer's disease, delirium, dementia, drug addiction, anorexia, and bulimia.

In another aspect, the invention includes a method of treating a disorder associated with an endothelial cell in a mammal, comprising administering to the endothelial cell of the mammal an isolated nucleic acid comprising a minigene, wherein said minigene encodes a modified carboxy terminal Gα peptide, or a modified carboxy terminal Gα peptide encoded thereby. According to this method, the peptide blocks a G protein-mediated signaling event in the endothelial cell, and thereby alleviates at least one symptom of the disorder associated with the endothelial cell in the mammal.

The invention additionally includes a composition comprising a peptide having an amino acid sequence selected from the group consisting of SEQ ID Nos: 39, 40, 41, 42, 43, 44, 45, 46, and 47.

Further, the invention includes a method of preventing conception in a female mammal. This method comprises administering to the female mammal either of a modified carboxy terminal Gα peptide or an isolated nucleic acid comprising a minigene, wherein the minigene encodes a modified carboxy terminal Gα peptide, thereby preventing conception in the female mammal.

BRIEF DESCRIPTION OF THE DRAWINGS

FIG. 2, comprising FIGS. 2A, 2B, and 2C, depicts the nucleotide sequences of representative minigenes, amino acid sequences of peptides encoded thereby, and amino acid sequences of representative Gα carboxy terminal peptides. FIG. 2A depicts the nucleotide sequences (SEQ ID NOs 1–14) of representative minigenes encoding Gα carboxy terminal peptides of the general formula, MGX, wherein X is an amino acid sequence corresponding the carboxy terminal region of a human Gα subunit. The portion of the nucleotide sequence depicted for each minigene includes a BamHI restriction endonuclease site, a ribosomal binding sequence, the translation initiation codon, methionine, a glycine codon, the nucleotide sequence encoding the Gα carboxy terminal peptide sequence of 11 amino acids, and the translation stop codon immediately downstream of the sequence encoding the peptide. FIG. 2B depicts the amino acid sequences (SEQ ID NOs. 15–29) of Gα carboxy terminal peptides encoded by representative minigenes. These peptides are of the general formula, MGX, wherein X is an amino acid sequence corresponding to the carboxy terminal region of a Gα subunit. FIG. 2C depicts the nucleotide sequences (SEQ ID NOs. 30–38) encoding the carboxy terminal regions of selected human Gα subunit proteins. FIG. 2D depicts the amino acid sequences (SEQ ID NOs. 39–47) of peptides corresponding to the carboxy terminal region of selected human Gα subunit proteins.

FIG. 3, comprising FIG. 3A is an image of a gel which depicts the separation of DNA fragments generated in a reverse transcription-polymerase chain reaction (RT-PCR) on a 1.5% agarose gel. FIG. 3B is a series of graphs which depicts the chromatograms resulting from an analysis of cytosolic extracts using high pressure liquid chromatography (HPLC).

FIG. 4, comprising

FIGS. 11A–D, is group of photographs depicting thrombin-induced stress-fiber formation in HMEC transiently transfected with pcDNA 3.1, pcDNA-Gα$_{12}$, or pcDNA-Gα$_{13}$.

DETAILED DESCRIPTION OF THE INVENTION

Figure 1:
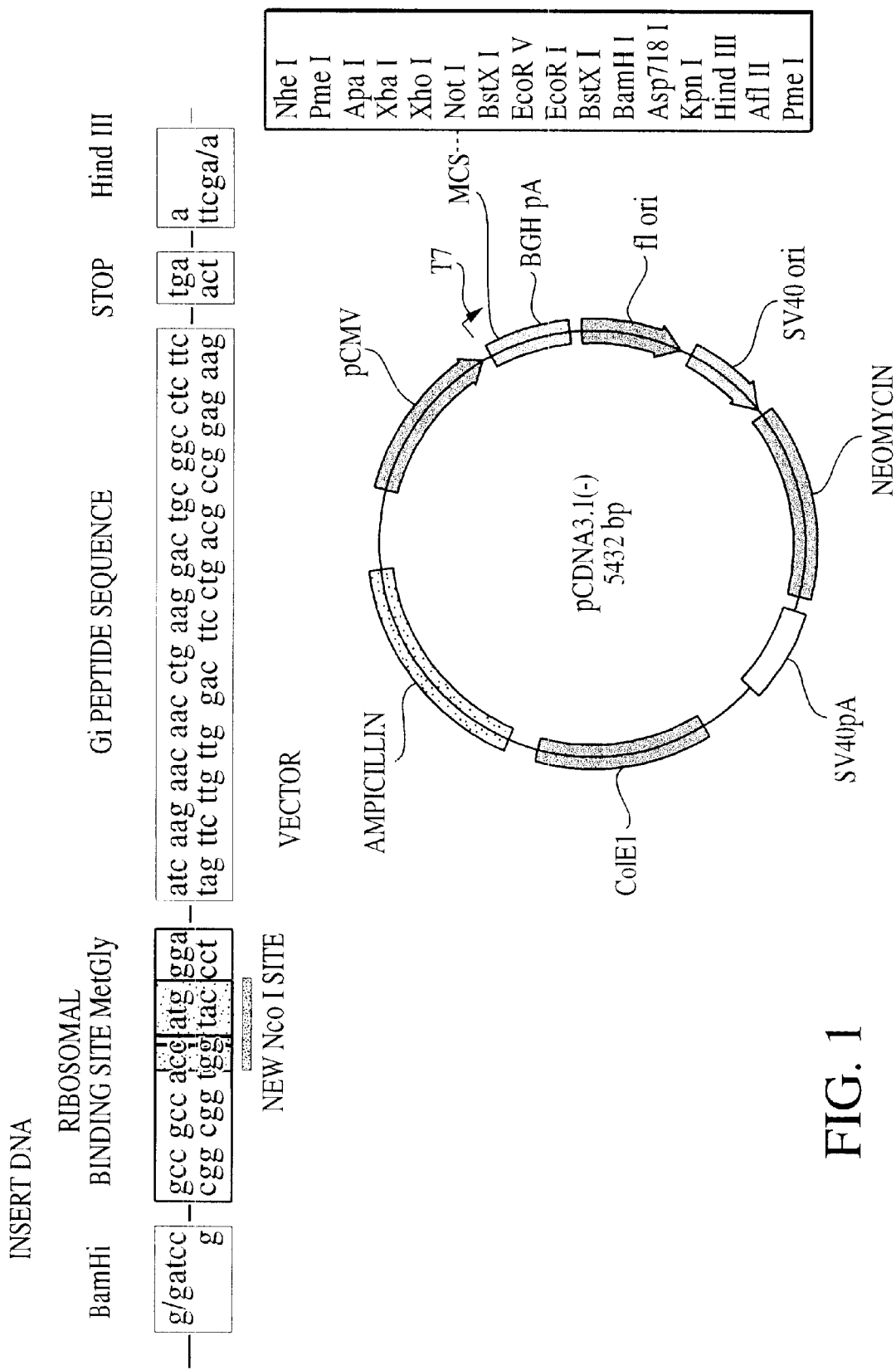
FIG. 1 is a diagram which depicts the design of a typical minigene and its insertion into the expression vector, pcDNA 3.1(Invitrogen; Carlsbad, Calif.).

The present invention encompasses compositions and methods useful for blocking G protein-mediated signaling events. The invention stems from the discovery that a peptide corresponding to the carboxy terminal region of a G protein α subunit (Gα) can interfere with the interaction between the G protein and its cognate receptor (GPCR), and thereby block subsequent signaling by the GPCR.

The present invention relates to carboxy terminal Gα peptides, and nucleotide sequences and minigenes which encode such peptides. The invention further relates to methods of making Gα peptide-encoding minigenes, and methods of using minigenes and the Gα carboxy terminal peptides encoded thereby, to block G protein-mediated signaling events. The invention additionally includes methods of using minigenes and the Gα carboxy terminal peptides encoded thereby for the identification of as yet unknown GPCR-G protein interactions, and for the treatment of pathological disorders associated with G protein-mediated signaling events.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Amplification" refers to any means by which a polynucleotide sequence is copied and thus expanded into a larger number of polynucleotide molecules, for example, by reverse transcription, polymerase chain reaction, or ligase chain reaction.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nuclcotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence.

Oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

A first region of an oligonucleotide "flanks" a second region of the oligonucleotide if the two regions are adjacent one another or if the two regions are separated by no more than about 1000 nucleotide residues, and preferably no more than about 100 nucleotide residues.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology. As further example, a "homolog" of a carboxy terminal Gα peptide is a peptide that is homologous in sequence, as defined herein, to a carboxy terminal Gα peptide.

As used herein, "homology" is used synonymously with "identity." Percent identity of one polynucleotide or polypeptide with respect to another polynucleotide or polypeptide may be determined using any available algorithm, such as the BLAST program.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g. as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 100 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences" or as being "upstream of" the reference point; sequences on the DNA strand which are 3' to a reference point on the DNA are referred to as "downstream sequences" or as being "downstream of" the reference point.

A "portion" of a polynucleotide means at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

As used herein, the term "promoter sequence" means a nucleic acid sequence which is required for expression of a gene product operably linked to the promoter sequence. In some instances, this sequence may be the core promoter sequence and in other instances, this sequence may also include an enhancer sequence and other regulatory elements which are required for expression of the gene product. The promoter sequence may; for example, be one which expresses the gene product in a tissue specific manner.

A "constitutive" promoter is one which is actively transcribed in a cell independent of the addition of an exogenous inducer agent. Similarly, a "constitutively activated" G protein receptor is a receptor which is actively initiating G protein-mediated signaling events independent of the addition of an exogenous inducing or stimulating agent As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "restriction endonuclease site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules of a similar type. By way of example, a G protein specifically binds a GPCR if the G protein substantially binds only that GPCR, and does not substantially bind other membrane receptors.

Conventional notation is used herein to refer to polypeptide and peptide amino acid sequences: the amino terminus of an amino acid sequence is the 5'-end; the the carboxy terminus of an amino acid sequence is the 3'-end. Amino acid sequences are listed herein from the 5' end to the 3' end of the sequence, as read left to right.

The terms "Gα carboxy terminal peptide" and "carboxy terminal Gα peptide" are used interchangeably herein. The terms "carboxy terminus" and "carboxy terminal region" of a "Gα subunit" or an "α subunit protein" are used herein to refer to the 3' end of an α subunit of a G protein. The sequence of "seven contiguous terminal amino acid residues" of a Gα subunit indicates the sequence of the seven contiguous amino acids at the 3' end of the Gα subunit amino acid sequence. By way of example, in a Gα subunit with the amino acid sequence of IKENLKDCGLF at the 3' end, the sequence of the seven contiguous terminal amino acid residues is -LKDCGLF.

Peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound as an anti-inflammatory agent, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acide analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting anti-inflammatory activity and these include, but are not limited to, substitution of one or more of the amino acids in the natural L-isomeric form with amino acids in the D-isomeric form. Thus, the peptide may include one or more D-amino acide resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitice, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use as an anti-inflammatory agent.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, "alleviating" a pathological disorder means reducing the severity of the symptoms of the pathological disorder.

As used herein, to "treat" means reducing the frequency with which symptoms of a pathological disorder are experienced by a mammal having the disorder.

Description

The present invention relates to an isolated nucleic acid comprising a minigene, wherein the minigene encodes a modified carboxy terminal Gα peptide. As exemplified in FIG. 1, a typical minigene of the invention can further comprise one or more of the following elements: a promoter sequence, a ribosome-binding nucleotide sequence, a methionine codon for translation initiation, an optional amino acid codon for stabilization of the translated peptide, a stop codon for translation termination, and a restriction endonuclease site. Alternatively, a minigene described herein can be incorporated into a vector, such as an expression vector, adjacent to one or more of a promoter sequence, a ribosome-binding nucleotide sequence, a methionine codon for translation initiation, an optional amino acid codon for stabilization of the translated peptide, a stop codon for translation termination, and a restriction endonuclease site.

The polynucleotide comprising the promotor sequence can be any polynucleotide comprising a promoter sequence, for example, and without limitation, the polynucleotide comprising the promoter sequence can be any viral-, bacterial-, yeast-, drosophila-, or mammalian-derived promoter sequence that is either known or becomes known, which is useful in the minigene of the invention. Suitable promoter sequences can include, but are not limited to, a T7 promotor, an Sp6 promotor, a cytomegalovirus (CMV) promotor, and a β-actin promotor.

The polynucleotide comprising the ribosome binding site may be any polynucleotide comprising ribosome binding site, for example, and without limitation, the polynucleotide comprising the ribosome binding site can be any viral-, bacterial-, yeast- or mammalian-derived ribosome binding site that is either known or becomes known, which is useful in the minigene of the invention.

In one embodiment, the minigene of the invention comprises a minigene sequence encoding a modified carboxy terminal Gα peptide having one of the following general formulas: MGX, MZX, or MX, wherein M is a methionine amino acid residue, G is a glycine amino acid residue, Z is an amino acid residue other than glycine, and X is a carboxy terminal Gα peptide sequence. By way of example, a minigene sequence of the invention can be any of the nucleotide sequences depicted in FIG. 2A (SEQ ID NOs: 1–14) which encode the peptide sequences depicted in FIG. 2B (SEQ ID Nos: 15–29). By way of further example, a minigene of the invention can comprise a nucleotide sequence, such as a sequence depicted in FIG. 2C (SEQ ID Nos: 30–38), which encodes a modified carboxy terminal Gα peptide having the formula MIX or MX, wherein I is an isoleucine amino acid residue and X is an amino acid sequence such as any one of SEQ ID Nos 39–47. In this embodiment, the modified carboxy terminal Gα peptide encoded by a minigene of the invention can comprise an amino acid sequence of the carboxy terminus of any Gα subunit which is known or becomes known, and can be any such peptide which exhibits the property of binding a G protein coupled receptor and is useful in the methods of the invention.

Included in the present invention is a minigene encoding a modified carboxy terminal Gα peptide comprising from at least about three contiguous amino acids to at least about 54 contiguous amino acids, and from at least about three contiguous amino acids to at least about eleven contiguous amino acids. By way of example, a preferred minigene can encode a modified peptide comprising at least about 13 contiguous amino acids such as any of the peptides depicted in FIG. 2B (SEQ ID Nos: 15–29) or FIG. 2D (SEQ ID Nos: 39–47). Nucleotide sequences of exemplary minigenes are depicted in FIG. 2A (SEQ ID Nos: 1–14).

A minigene of the invention should not be construed to be limited solely to encoding a carboxy terminal Gα peptide disclosed herein. Rather, the invention should be construed to include a minigene which encodes any amino acid sequence that shares substantial homology with the amino acid sequence of a Gα carboxy terminal peptide sequence which is known or becomes known. For example, the invention can include a minigene which encodes a modified carboxy terminal Gα peptide comprising contiguous amino acids of a length described herein which is at least about 90%, more preferably, at least about 95%, and most preferably, at least about 99% identical to the amino acid sequence of the carboxy terminal region of a Gα subunit protein, and which includes at least the seven contiguous terminal residues of the a subunit protein. By way of further example, the invention can include a minigene which encodes a peptide having an amino acid sequence which is at least about 90%, more preferably, at least about 95%, and even more preferably, at least about 99% identical to the amino acid sequence of the carboxy terminal region of a Gα subunit protein, and including at least the seven contiguous terminal amino acid residues of a carboxy terminal Gα peptide disclosed herein (SEQ ID Nos: 15–29 and 39–47).

A minigene described herein is assembled using ordinary molecular biology techniques, such as those described, for example, in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. eds. (1994, Methods for General and Molecular Bacteriology, American Society for Microbiology, Washington, D.C.). Accordingly, the design of minigene functional elements such as a stop codon and any appropriate restriction endonuclease sites, is understood to be within the ability of one skilled in the art of molecular biology. Upon reading the present disclosure and examining the particulars of FIG. 1 provided herein, it is a simple matter for the skilled artisan to construct a minigene such that it can be useful for the methods of the present invention. By simply substituting a desired minigene sequence in place of the minigene sequence shown in FIG. 1, it is a simple matter to construct a minigene encoding any desired Gα carboxy terminal peptide.

In various embodiments, the invention includes a vector comprising a minigene of the invention. The vector can be used to introduce a minigene encoding a carboxy terminal Gα peptide into a cell. Any type of vector known in the art is suitable for this purpose, including without limitation, plasmid based vectors, viral based vectors, and non-DNA vectors. Examples of suitable plasmid based vectors include, without limitation, any plasmid which comprises sequences capable of facilitating either of propagation and expression of the desired gene in a prokaryotic or eukaryotic cell. Examples of suitable viral vectors include, but are not limited to, retroviral vectors, adenoviral vectors, and adeno-associated viral vectors. Examples of non-DNA vectors include, without limitation, polylysine compounds, liposomes, and the like. In preferred embodiments, the vector comprising a minigene of the invention is an expression vector.

The invention additionally includes modified carboxy terminal Gα peptides having one of the following general formulas: MGX, MZX, or MX, wherein M is a methionine amino acid residue, G is a glycine amino acid residue, Z is an amino acid residue other than glycine, and X is a carboxy terminal Gα peptide sequence. By way of example, a modified carboxy terminal Gα peptide can comprise any of the amino acid sequences depicted in FIG. 2B (SEQ ID NOs: 15–29). By way of further example, a modified carboxy terminal Gα peptide of the invention can have the general formula MAX or MX, wherein A is an alanine amino acid residue and X is an amino acid sequence, such as any of SEQ ID Nos 39–47. In this embodiment, the modified carboxy terminal Gα peptide of the invention can comprise an amino acid sequence of the carboxy terminus of any Gα subunit which is known or becomes known, and can be any such peptide which exhibits the property of binding a G protein coupled receptor and is useful in the methods of the invention.

In preferred embodiments, modified carboxy terminal Gα peptides of the invention comprise from at least about three contiguous amino acids to at least about 54 contiguous amino acids, from at least about three contiguous amino acids to at least about eleven contiguous amino acids, and at least about eleven contiguous amino acids. In a most preferred embodiment, a carboxy terminal Gα peptide comprises an amino acid sequence which is homologous to the amino acid sequence of at least the seven contiguous terminal amino acid residues of the carboxy terminal region of a Gα subunit protein. By way of example, the invention includes a peptide such as SEQ ID NO: 15 which comprises thirteen contiguous amino acids, within which is the 5' modification of a methionine amino acid residue and a glycine amino acid residue, and the seven contiguous terminal residues, -G-L-F-, of the 3' end (i.e. the carboxy terminus of the peptide) which are homologous to the seven contiguous terminal amino acid residues of the α subunit of the G protein, transducin (Gα$_t$). By way of further example, a modified carboxy terminal Gα peptide of the invention can be any of the peptides depicted in FIG. 2B (SEQ ID NOs: 15–29).

The invention further encompasses a peptide corresponding to the carboxy terminal region of any Gα subunit which is known or becomes known, and which exhibits the property of binding a G protein coupled receptor. In preferred embodiments, such carboxy terminal Gα peptides comprise from at least about three contiguous amino acids to at least about 54 contiguous amino acids, from at least about three contiguous amino acids to at least about eleven contiguous amino acids, and at least about eleven contiguous amino acids. In a most preferred embodiment, a carboxy terminal Gα peptide of the invention comprises an amino acid sequence which is homologous to the amino acid sequence of at least the seven contiguous terminal residues of the carboxy terminal region of a Gα subunit protein. By way of example, a peptide of the invention can be any of the peptides depicted in FIG. 2D (SEQ ID NOs: 39–47).

A carboxy terminal Gα peptide of the invention should not be construed to be limited solely to encoding a carboxy terminal Gα peptide disclosed herein. Rather, the invention should be construed to include any peptide comprising an amino acid sequence which shares substantial homology with the carboxy terminal amino acid sequence of a Gα subunit protein which is known or becomes known. For example, the invention can include a peptide comprising contiguous amino acids of a length described herein which is at least about 90%, more preferably, at least about 95%, and even more preferably, at least about 99% identical to the amino acid sequence of the carboxy terminal region of a Gα subunit protein including at least the seven contiguous terminal amino acid residues of the α subunit protein. By way of further example, the invention can include a minigene which encodes a carboxy terminal Gα peptide or modified carboxy terminal Gα peptide having an amino acid sequence which is at least about 90%, more preferably, at least about 95%, and even more preferably, at least about 99% identical to the amino acid sequence of a carboxy terminal Gα peptide or modified carboxy terminal Gα peptide disclosed herein (SEQ ID Nos: 15–29 and 39–47).

The invention encompasses any carboxy terminal Gα peptide or modified carboxy terminal Gα peptide which is encoded by a nucleic acid, such as, a minigene, as well as a carboxy terminal Gα peptide or modified carboxy terminal Gα peptide which is generated synthetically or biosynthetically. Any method of peptide synthesis or biosynthesis available to a skilled artisan can be employed in preparing peptides useful for the methods described herein.

In alternative embodiments, a Gα carboxy terminal peptide, such as any of SEQ ID Nos: 30–39, can be useful for the methods described herein.

The invention includes a cell comprising a minigene, a modified carboxy terminal Gα peptide, or a carboxy terminal Gα peptide of the invention. Such a cell can be prokaryotic or eukaryotic. For example, the cell can be a yeast cell, a bacterial cell, an insect cell, a xenopus cell, a drosophila cell, or a mammalian cell. In addition, the cell having a minigene introduced therein, can be one which resides in a mammal (i.e. in vivo), or alternatively, can be a cell in culture (i.e. in vitro).

The invention also encompasses pharmaceutical compositions useful in the methods of the invention. Such compositions included in the present invention are now described.

The invention encompasses the preparation and use of pharmaceutical compositions comprising one of a minigene encoding a Gα carboxy terminal peptide, a peptide encoded thereby, and a Gα carboxy terminal peptide otherwise generated as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient.

The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or N-propyl-p-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 $\mu$g to about 100 g per killogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per killogram of body weight of the animal. More preferably, the dosage will vary from about 10 mg to about 1 g per killogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, including, but not limited to, the type and severity of the disease being treated, the type and age of the animal, etc.

Methods of using any of a minigene encoding a modified carboxy terminal Gα peptide, a modified peptide encoded thereby, and a modified carboxy terminal Gα peptide otherwise generated, are now described.

The carboxy terminal peptide of a Gα subunit can be used to inhibit any reaction that requires signaling by a G protein coupled receptor (GPCR). Known examples of GPCRs for which such inhibition could be useful include, without limitation, a wide range of biologically active receptors, such as hormone receptors, viral receptors, growth factor receptors, chemokine receptors, sensory receptors, and neuroreceptors.

Accordingly, the invention includes a method of using a modified carboxy terminal Gα peptide to inhibit a G protein-mediated signaling event in a cell. This method comprises administering to a cell an isolated nucleic acid comprising a minigene which encodes a modified Gα carboxy terminal peptide. Alternatively, the method comprises administering to the cell a modified Gα carboxy terminal peptide described herein, having the property of binding a G protein coupled receptor. By way of example, the method of inhibiting a G protein-mediated signaling event in a cell can include administering to the cell any of the minigenes, SEQ ID NOs 1–14, or any of the peptides, SEQ ID NOs 15–29 and 39–47. This method can optionally be useful for inhibiting G protein-mediated signaling events in a cell associated with constitutively activated GPCRs, and antibody-crosslinked irreversibly activated GPCRs.

The invention also includes a method of blocking the site of interaction between a G protein and a G protein coupled receptor in a cell. This method comprises administering to a cell either of a minigene or a modified carboxy terminal Gα peptide, such that the modified carboxy terminal Gα peptide, either administered to the cell or expressed from an administered minigene, blocks the site of interaction between the G protein and the G protein coupled receptor in the cell.

Additionally, the present invention includes a method of using a minigene or modified carboxy terminal Gα peptide encoded thereby to identify which G protein specifically binds a particular GPCR. This method is useful for identifying which family of G proteins (i.e. $G_i$, $G_s$, $G_t$, $G_q$, etc.) specifically binds a known or newly discovered GPCR whose G protein partner is not known (i.e. an orphan receptor). Examples of such GPCRs include, but are not limited to, TSH receptors, which are important in Graves Disease, and proteinase activated receptors (PARs). This method comprises administering to the cell a minigene of the invention or a modified carboxy terminal Gα peptide encoded thereby, and assessing the level of occurrence of a G protein-mediated signaling event associated with either the particular GPCR or a particular G protein. The assessment can be performed as described herein, or in any other manner which is useful in the methods of the invention.

The method of identifying which G protein binds a particular GPCR in a cell further comprises comparing the level of occurrence of a signaling event associated with the GPCR in a cell to which a minigene or a modified carboxy terminal Gα peptide of the invention has been administered, with the level of occurrence of that signaling event in a comparable cell to which the minigene or peptide has not been administered. In this embodiment, a measurable reduction in the level of occurrence of the signaling event in the cell to which the minigene or modified peptide has been administered compared with the level of occurrence of that signaling event in a cell to which the minigene or modified peptide has not been administered, is an indication that the modified carboxy terminal Gα peptide expressed from the minigene or administered to the cell as a peptide, binds the particular GPCR involved in the signaling event.

A modified carboxy terminal Gα peptide which is useful in the method described above can comprise an amino acid sequence which is homologous with at least the seven contiguous terminal amino acid residues of a Gα subunit protein. Accordingly, a modified carboxy terminal Gα peptide that exhibits the ability to bind a particular GPCR and decrease the level of occurrence of a signaling event in which the GPCR is involved, identifies the G protein with which the Gα carboxy terminal peptide shares amino acid sequence homology as being the G protein that specifically binds the particular GPCR involved in the signaling event.

In other embodiments, the invention includes methods of inhibiting in a cell one or more of migration, permeability and proliferation. In these embodiments, the method comprises administering to the cell either a minigene or a modified carboxy terminal Gα peptide, thereby inhibiting migration, permeability, proliferation, or a combination thereof in a cell.

The methods described herein can further comprise assessing the level of occurrence of a particular signaling event in the cell following the administration of a minigene or a modified carboxy terminal Gα peptide. This assessment of a signaling event can, for example, include pretreatment of the cell with one or more stimulating agents (i.e. ligands which bind GPCRs, thereby inducing interaction with their cognate G proteins), and measuring downstream events which are the consequence of a signaling event to be assessed. By way of example, the level of occurrence of a signaling event involving the GPCR, PAR-1, can be assessed by treating the cell with thrombin, which stimulates PAR-1, and measuring a downstream event that results from signaling by PAR-1, such as an accumulation in the cell of inositol phosphate or an increase of mitogen-activated protein kinase activity in the cell.

The methods described herein include administering an isolated, nucleic acid or a composition described herein to a cell which can be a prokaryotic cell or a eukaryotic cell, and which can be in culture or in the body of a mammal. Examples of the type of cell to which a minigene or modified peptide of the invention can be administered in the above methods include, but, are not limited to, a mammalian cell, such as a human cell, and specific cell types thereof, such as an endothelial cell, a neuronal cell, a myocardial cell, and the like.

In reference to the methods of the invention, protocols which can be useful for administering to a cell either an isolated nucleic acid or a peptide composition, and which are not described herein are well known and within the competence of one of ordinary skill in the art of cell culture.

The present invention additionally relates to methods which involve administering a minigene or modified peptide described herein to a mammal. In reference to these methods, a minigene, a modified peptide, or a pharmaceutical composition comprising either a minigene or modified peptide described herein can be administered to a mammal, preferably a human. The relevant pharmacological factors involved in administering these agents are either described in previous sections or are well known in the art and within the competence of a skilled artisan.

G protein-mediated signaling events are associated with or have been implicated as being responsible for many pathological disorders in animals and humans. For example, aberrant G protein signaling can be involved in the pathology associated with processes involving inflammation, various infections, disease processes, such as those affecting the cardiopulmonary, endocrine, reproductive, digestive, nervous, and immune systems, and connective and vascular tissues, and surgical complications, such as those following vascular surgery, coronary bypass surgery, abdominal surgery, and organ transplant surgery. However, methods of treating such disorders have not been apparent until the present invention.

Accordingly, the invention includes a method of treating a pathological disorder in a mammal. This method can comprise, for example, administering to the mammal any of a minigene encoding a Gα carboxy terminal peptide which is known or becomes known, and a modified peptide encoded thereby or otherwise produced, capable of blocking a G protein mediated signaling event associated with the pathological disorder. Preferably, a minigene or peptide of the invention is administered in an amount sufficient to inhibit the G protein-mediated signaling event associated with the pathological disorder. Also preferred is administration of either a minigene or peptide of the invention which results in the alleviation of at least one symptom of the pathological disorder.

The invention encompasses a method of treating a condition for which an association with a G protein mediated signaling event is known or becomes known. By way of example, an orphan receptor for which a G protein partner is identified, and with which a pathological disorder becomes associated, can be blocked according to the method described to treat the associated pathological condition.

Examples of pathological disorders which can be treated using the method described herein include, but are not limited to, stroke, myocardial infarction, restenosis, atherosclerosis, hypotension, hypertension, angina pectoris, acute heart failure, cardiomyocyte apoptosis, cancers, bacterial infections, fungal infections, protozoan infections, viral infections, septic shock, pain, chronic allergic disorders, asthma, inflammatory bowel disease, osteoporosis, rheumatoid arthritis, Grave's disease, postoperative ilcus, diabetes, adult respiratory distress syndrome, myasthenia gravis, cardiovascular disease, congestive heart failure, Chagas disease, disorders associated with solid organ transplant, vascular sclerosis, chronic rejection, chronic obstructive pulmonary disease, urinary retention, testotoxicosis, infertility, ulcers, obesity, benign prostatic hypertrophy, anxiety, epilepsy, schizophrenia, manic depression, Parkinson's disease, Alzheimer's disease, delirium, dementia, drug addiction, anorexia, and bulimia.

G protein mediated signaling events have been associated with various reproductive functions in mammals (Flanagan et al., 1997, Rev. Reprod. 2:113–120; Gromoll et al., 1996; Mol. Cell Endocrinol. 125:177–82; Inanobe et al., 1999, J. Physiol. (Lond) 521 :19–30). However, methods of modulating reproduction by manipulating G protein mediated signaling have not been apparent until the present invention.

Accordingly, the present invention includes a method of preventing conception in a mammal. This method comprises.administering to a female either of an isolated nucleic acid comprising a minigene which encodes a modified carboxy terminal Gα peptide, or a modified carboxy terminal Gα peptide, thereby preventing conception in the female mammal. The administration of such a contraceptive can be carried out using any methods described in previous sections or any well known methods which are within the competence of one skilled in the art.

The invention is now described with reference to the following Examples. These Examples are provided for the purpose of illustration only and the invention is not limited to these Examples, but rather encompasses all variations which are evident as a result of the teaching provided herein.

EXAMPLES

The experiments presented in the following Examples illustrate the construction of a minigene of the invention and the use of selected minigenes to inhibit G protein-mediated signaling events.

Example 1

Construction of Minigenes

Construction of the minigenes was performed using standard reagents and molecular cloning techniques. The functional organization of the minigenes described in this example is illustrated in FIG. 1. Two DNA components of the minigenes, insert DNA and vector DNA, were prepared separately.

Insert DNA was prepared by first annealing complementary oligonucleotides comprising, from 5' to 3', a BamH1 restriction endonuclease site, a ribosome-binding nucleotide sequence, a methionine codon for initiating translation of the subsequent peptide sequence, a glycine codon for stabilization of the translated peptide, a nucleotide sequence encoding a Gα carboxy terminal peptide, a stop codon for translation termination, and a Hind III restriction endonuclease restriction site. The 56 bp oligonucleotides were ordered from Great American Gene Company (Ramona, Calif.) with their 5' ends phosphorylated. DNA oligonucleotides were annealed by placing them at 85° C. for 5 minutes before allowing them to cool to room temperature slowly. Examples of insert DNA nucleotide sequences are depicted in FIG. 2.

Vector DNA was prepared by restriction endonuclease digestion of the commercially available pcDNA 3.1 plasmid vector (Invitrogen; Carlsbad, Calif.) using BamH1 and HindIII restriction endonucleases. After digestion with each restriction enzyme the pcDNA 3.1 plasmid vector was run on an 0.8% agarose gel, the appropriate band cut out, and the DNA purified (QIAquick Gel Extraction Kit, QIAGEN, Valencia, Calif.).

The annealed cDNA oligonucleotides were ligated for 1 hour at RT into pcDNA 3.1 plasmid vector (Invitrogen; Carlsbad, Calif.) previously cut with BamHI and Hind111. For the ligation reaction the ratio of insert to vector was approximately 25 μM to 50 ng. Respectively. Following ligation, the samples were heated to 65° C. for 5 minutes to deactivate the T4 DNA ligase (New England Biolabs, Beverly, Mass.). Electrocompompetent *E. coli.* (strain AR1814) were electroporated in the presence of the resulting ligated insert-vector DNA.

Plasmid DNA was recovered from bacteria and purified using the QIAprep Miniprep System (QIAGEN; Valencia, Calif.). The presence of the insert DNA in the purified plasmid DNA was confirmed by performing restriction analysis using NcoI restriction endonuclease. Restriction analysis consisted of digesting purified plasmid DNA with NcoI using standard conditions and reagents, followed by electrophoresis of the digested DNA through a 1.5% agarose gel matrix.

Figure 3A:
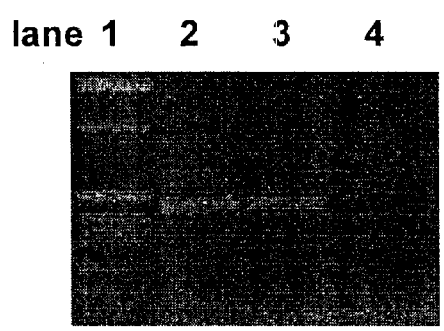
FIGS. 3A and 3B, depicts analyses of minigene expression in transiently transfected HEK 293 cells.
Figure 3B:
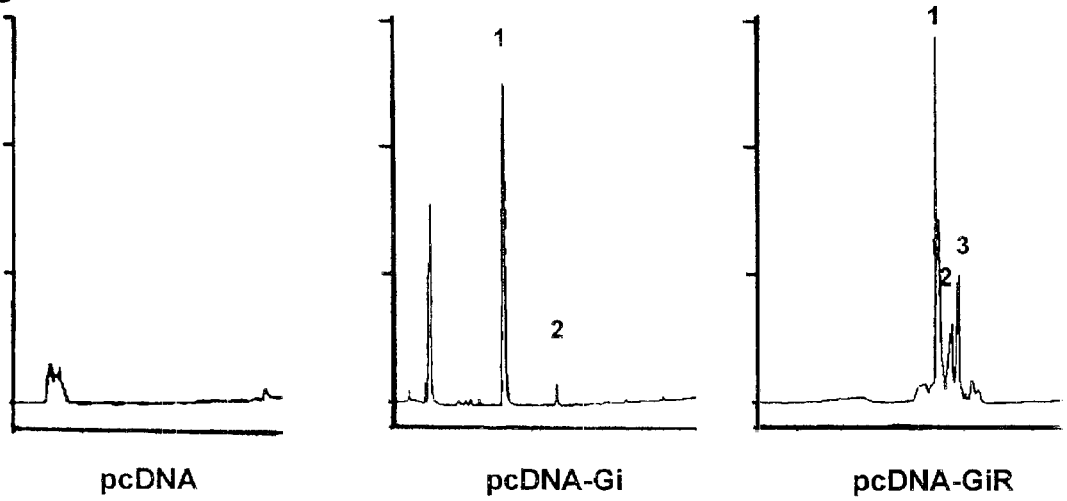

The results of restriction analysis of purified plasmid DNA are shown in FIG. 3. Lane 1 in FIG. 3 is a 1-kilobase pair DNA ladder used as a molecular weight standard. The presence of the insert DNA in the digested plasmid DNA sample is indicated by a pattern of four DNA fragments, shown in FIG. 3 for minigene plasmids pcDNA-Gα$_i$ (lane 3), pcDNA-Gα$_i$R (lane 4), and pcDNA-Gα$_q$ (lane 5). The absence of the insert DNA is indicated by a pattern of three DNA fragments, as seen with the pcDNA 3.1 plasmid vector in lane 2 of FIG. 3.

Example 2

Transfection and Expression of Minigenes in Cells

The experiments of this example describe the transfection of HEK 293 cells with minigene DNA and the analysis of the expression of minigene DNA and translation products thereof in transfected cells.

Transfection of Cells and Analysis of Total Cell RNA from Transfected Cells

Figure 4A:
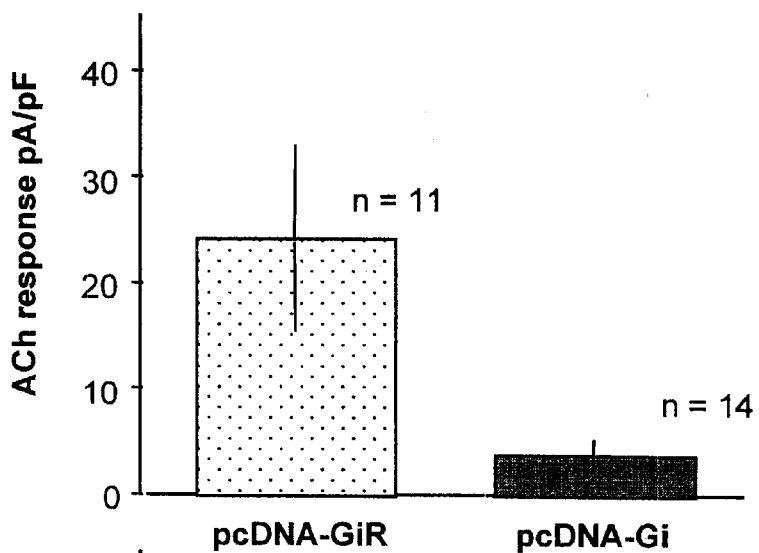
FIGS. 4A, 4B, and 4C, is a series of graphs which depicts a comparison of the acetylcholine (Ach) activation of inwardly rectifying potassium channels (GIRKs) in HEK 293 cells transiently transfected with selected minigenes.

Transfection of HEK 293 cells with the minigene constructs, pcDNA-Gα$_i$R and pcDNA-Gα$_i$, and the control construct, pcDNA 3.1, was carried out using calcium phosphate. Total RNA was isolated from transfected cells 48 hours post-transfection using a Qiagen Rneasy Kit and QIAshredder (Qiagen, Valencia, Calif.). The isolated total cell RNA was used as the template in a reverse transcription-polymerase chain reaction (RT-PCR) with commercially available reagents and methods (Clonetech Advantage RT for PCR kit; Clontech, Palo Alto, Calif.) to generate the corresponding cDNA. The cDNA was then used as the template in a standard PCR with primers complementary to the nucleotide sequence of a portion of the insert DNA described in Example 1. PCR products obtained using this procedure were analyzed using electrophoresis through a 1.5% agarose gel matrix. A typical analysis of this type is depicted in FIG. 4A. Lane 1 is a 1 kilobase DNA ladder. Lane 2 is a PCR product obtained with cells transfected with pcDNA-Gα$_i$R. Lane 3 is a PCR product obtained with cells transfected with pcDNA-Gα$_i$. Lane 4 is a PCR product obtained with cells transfected with pcDNA3.1.

Analysis of Gα Carboxy Terminal Peptide Expression in Transfected Cells

Figure 4B:
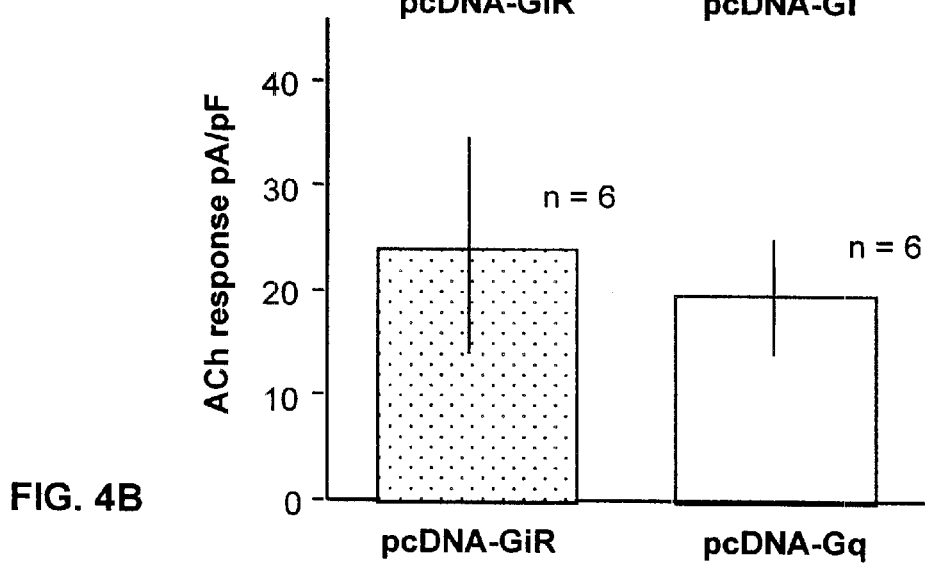

HEK-293 cells transfected with the minigene constructs, pcDNA-Gα$_i$R and pcDNA-Gα$_i$, and the control construct, pcDNA 3.1, were lysed and homogenized 48 hour post-transfection using conventional methods. The resulting cytosolic extracts were analyzed using high pressure liquid chromatography (HPLC). Eluent corresponding to individual peaks observed in HPLC analyses was analyzed by ion mass spray analysis. HPLC chromatograms of cytosolic extracts from cells transfected with the minigene constructs, pcDNA-Gα$_i$R and pcDNA-Gα$_i$, and the control construct, pcDNA 3.1, are shown in FIG. 4B. The ion mass spray analysis for peak 1 from cells transfected with pcDNA-G$_i$ and peak 1 from cells transfected with pcDNA-G$_i$R indicate the presence of a 1450 dalton peptide, i.e. the expected molecular weight for each of the 13 amino acid peptide sequences encoded by the minigenes. A comparable peak is absent in the cytosolic extract from cells transfected with the control construct.

The results of the experiments of this example indicate that, in transiently transfected HEK 293 cells, the minigenes are present, and the Gα carboxy terminal peptides encoded by the minigenes are expressed.

Example 3

Blockade of G Protein-Mediated Signaling Events by Minigenes

The experiments of this Example illustrate the use of minigenes as effective and specific blockers of G protein-mediated signaling events. The general approach of these experiments is as follows. Transient transfection of cells with selected minigene DNA is followed by exposure of transfected cells to a specific G protein coupled receptor (GPCR) agonist and subsequent measurement of appropriate cellular responses associated with stimulation by the agonist.

Minigenes selected for these experiments include pcDNA-Gα$_i$, pcDNA-Gα$_s$, pcDNA-Gα$_q$, and the random order minigene, pcDNA Gα$_i$R. Also included is the vector DNA, pcDNA 3.1, which does not contain minigene insert DNA. Preparation of these minigenes was carried out as described in Example 1.

Inhibition of Muscarinic M$_2$ Receptor (M$_2$ mAchR) Activation of Inwardly Rectifying Potassium Channels (GIRKs)

G protein regulated GIRK channels modulate electrical activity in excitable cells. A GIRK channel opens as a consequence of a direct interaction with the Gβγ portion of a G protein. Thus, a whole cell patch clamp recording of inwardly rectifying K$^+$ currents can be used as a measure of G protein activity in single intact cells. In this type of experiment, a Gα$_i$ carboxyl terminal peptide minigene is being tested for its ability to inhibit M$_2$ mAChR activation of inwardly rectifying K$^+$ currents, that is, the ability to block the interaction between a GIRK channel, the G protein coupled receptor (GPCR), and its cognate G protein, G$_i$.

HEK 293 cells were transiently transfected with plasmid DNA encoding GIRK1/GIRK4 channel proteins and DNA comprising one of the minigenes, pcDNA-Gα$_i$, pcDNA-Gα$_s$, pcDNA-Gα$_q$, and pcDNA-Gα$_i$R. After 48 hours of transfection, the cells were superfused with 1 micromolar acetylcholine (Ach). Measurement of whole cell currents to determine the level of G protein mediated signaling activity in cells was performed as follows. Membrane currents were recorded under voltage clamp using conventional whole cell-patch techniques. Variables arising from transfection and culture conditions were minimized by performing control minigene transfections (i.e. with pcDNA-Gα$_i$R) in parallel with pcDNA-Gα$_i$, pcDNA-Gα$_s$, and pcDNA-Gα$_q$ minigene transfections. For analysis of the data the maximal current density (peak amplitude) of ACh-induced inwardly rectifying K$^+$ currents were measured at −80 millivolts and compared. Summarized data for the maximum amplitude of ACh evoked currents are shown in FIG. 4 for selected transfection conditions.

As shown in FIG. 4, cells transfected with pcDNA-Gα$_i$ DNA exhibited a dramatically impaired response to agonist stimulation of M$_2$ mAchR. The data in FIG. 4A demonstrate that superfusion of the cells with ACh activated inwardly rectifying K$^+$ currents in cells transfected with pcDNA-Gα$_i$R DNA but did not activate inwardly rectifying K$^+$ currents in cells transfected with pcDNA-Gα$_i$ DNA. Thus, the pcDNA-Gα$_i$ minigene completely blocked the agonist-stimulated GIRK1/4 response while the random order minigene, pcDNA-Gα$_i$R, which should not have a specific affinity for M$_2$ mAchR, did not block the agonist-stimulated GIRK1/4 response.

Figure 4C:
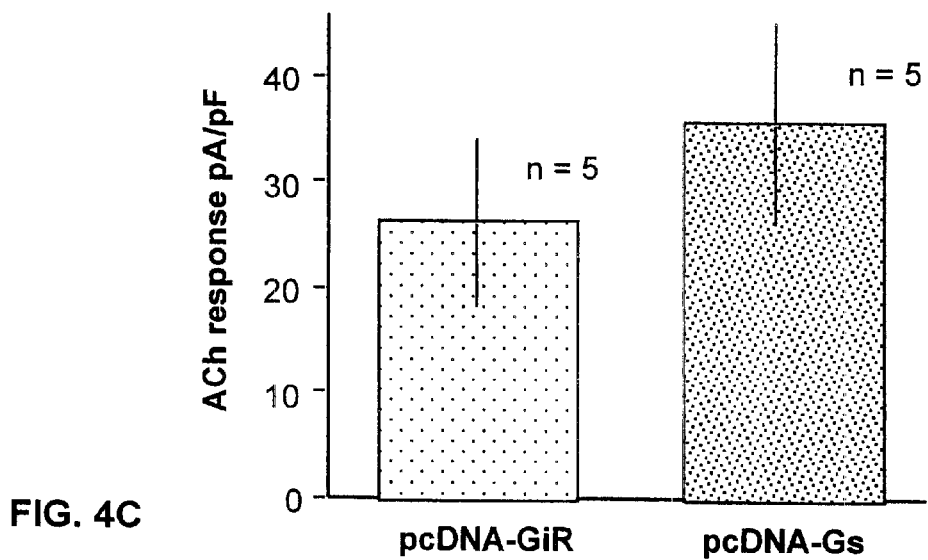

The data in FIGS. 4B and 4C demonstrate that the agonist-stimulated GIRK1/4 response, i.e. the activation of inwardly rectifying K$^+$ currents, in cells transfected with either of the minigenes, pcDNA-Gα$_s$ and pcDNA-Gα$_q$, was not significantly different than the agonist-stimulated GIRK1/4 response of cells transfected with the control minigene, pcDNA-Gα$_i$R. Therefore, the transfection of cells with minigene DNA encoding the carboxy terminal peptides of Gα$_s$ and Gα$_q$, i.e. peptides derived from G proteins that do not normally interact with GIRK channels, does not result in a blockade of the agonist-stimulated GIRK1/4 response in cells.

The results of these experiments taken together indicate that the GIRK1/4 G protein coupled response is effectively and specifically blocked by transfection with pcDNA-G$\alpha_i$ minigene DNA (Gilchrist et al., 1999, J. Biol. Chem. 274: 6601–6606).

Blockade of G Protein-mediated Signaling Events Involving the PAR-1 Receptor

The thrombin receptor, PAR-1, is expressed in endothelial cells, and has been reported to activate multiple G proteins. Because PAR-1 interacts with multiple G proteins, there are a number of experimental endpoints which can be used as measures of PAR-1 signaling events. The experiments which follow demonstrate the effect on thrombin-stimulated PAR-1 signaling of transiently transfecting HMEC with selected minigenes and a control DNA and measuring induction of PAR-1 gene expression, intracellular $CA^{2+}$ levels, intracellular cAMP levels, MAPK activity, inositol phosphate accumulation, and endothelial cell permeability, proliferation, stress fiber formation, and adhesion.

a. Blockade of Thrombin-Stimulated Decreases in cAMP Accumulation

Isoproterenol serves as an agonist for the GPCR β-adrenergic receptor. When stimulated by isoporterenol, β-adrenergic receptors activate their cognate proteins ($G_S$) which subsequently stimulate adenylyl cyclase and lead to significant increases in cellular levels of cyclic adenosine monophosphate (cAMP). Thrombin receptor (PAR1) is known to couple to multiple G proteins, including $G_i$. The measurement of cAMP levels as an indicator of thrombin-stimulated PAR-1 signaling was carried out as follows. HMEC were seeded onto 6-well culture dishes at $1 \times 10^5$ cells per well at least 24 hours before transfection. The plated cells were transiently transfected with either the empty vector control DNA, pcDNA3.1, or one of the minigene DNAs, pcDNA-G$\alpha_{i1/2}$, and pcDNA-G$\alpha_i$R, at a concentration of 1 microgram of DNA per well. Transfections were performed using Effectene and the accompanying protocols (Qiagen, Valencia, Calif.). At 24 hours post-transfection, cells were treated with tritium-labeled adenine having a specific radioactivity of 3 microcuries per milliliter ([$^3$H]-adenine). 24 hours later, cells were washed once with a solution comprising 1 millimolar isobutylmethylxantine in serum-free media. Cells were subsequently treated with a solution comprising 1 micromolar isoproterenol in serum-free media for 30 min at 37° C. to stimulate cAMP production. For thrombin inhibition reactions, cells were exposed to either of a solution comprising 50 nanomolar thrombin and a solution comprising 1 micromolar quinpirole for at least 15 minutes prior to the treatment with the isoproterenol solution. Cell treatments were terminated by aspiration of the treatment solution followed by addition of an ice cold solution comprising 5% trichloroacetic acid. The assessment of cAMP accumulation in cells was carried out by separation of the acid-soluble nucleotides on ion-exchange columns.

Figure 5:
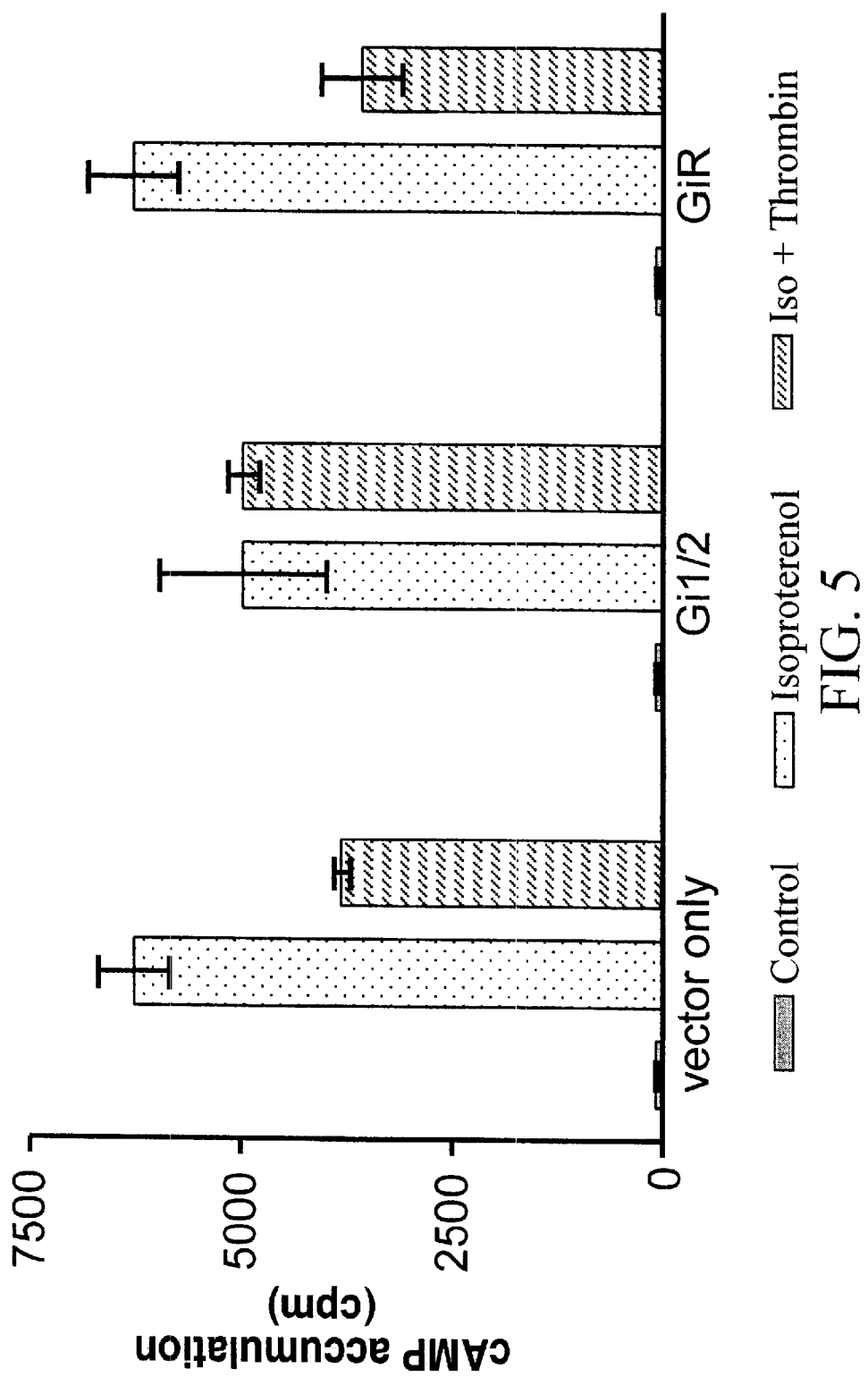
FIG. 5 is a graph which depicts a comparison of the level of cyclic adenosine monophosphate (cAMP) accumulation in human microvascular endothelial cells (HMEC) transiently transfected with pcDNA 3.1, (vector only), pcDNA-Gα$_{i1/2}$ (Gi1/2), or pcDNA-Gα$_i$R (GiR). The cells are stimulated with either isoproterenol or both isoproterenol and thrombin. Control cells are not stimulated.
Figure 13:
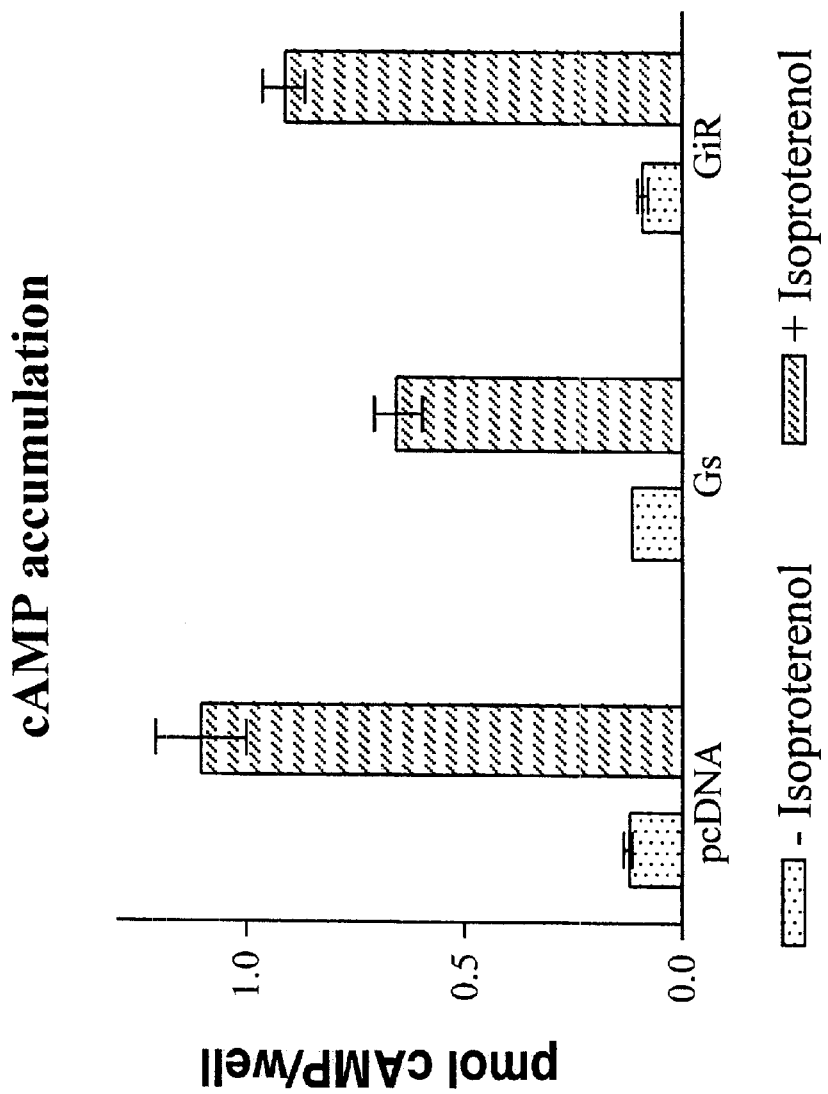
FIG. 13 is a graph which depicts a comparison of the level of cyclic adenosine monophophate (cAMP) accumulation in HMEC transiently transfected with pcDNA 3.1, pcDNA-Gα$_s$, or pcDNA-Gα$_i$R. The cells are stimulated with isoproterenol which generates cAMP via activation of β-adrenergic receptors.

The results of these experiments are depicted in FIGS. 5 and 13, and are expressed as (cAMP/cAMP+ATP)×1000 for each of cells transfected with pcDNA3.1, cells transfected with pcDNA-G$\alpha_{i1/2}$, and cells transfected with pcDNA-G$\alpha_i$R. The isoproterenol-stimulated increase in cAMP accumulation was inhibited by thrombin treatment in cells transfected with either pcDNA 3.1 or pcDNA-G$\alpha_i$R DNA. In contrast, treatment with thrombin did not inhibit isoproterenol-stimulated cAMP accumulation in cells transfected with pcDNA-G$\alpha_{i1/2}$ DNA.

b. Inhibition of Thrombin-Stimulated Proliferation

Figure 6:
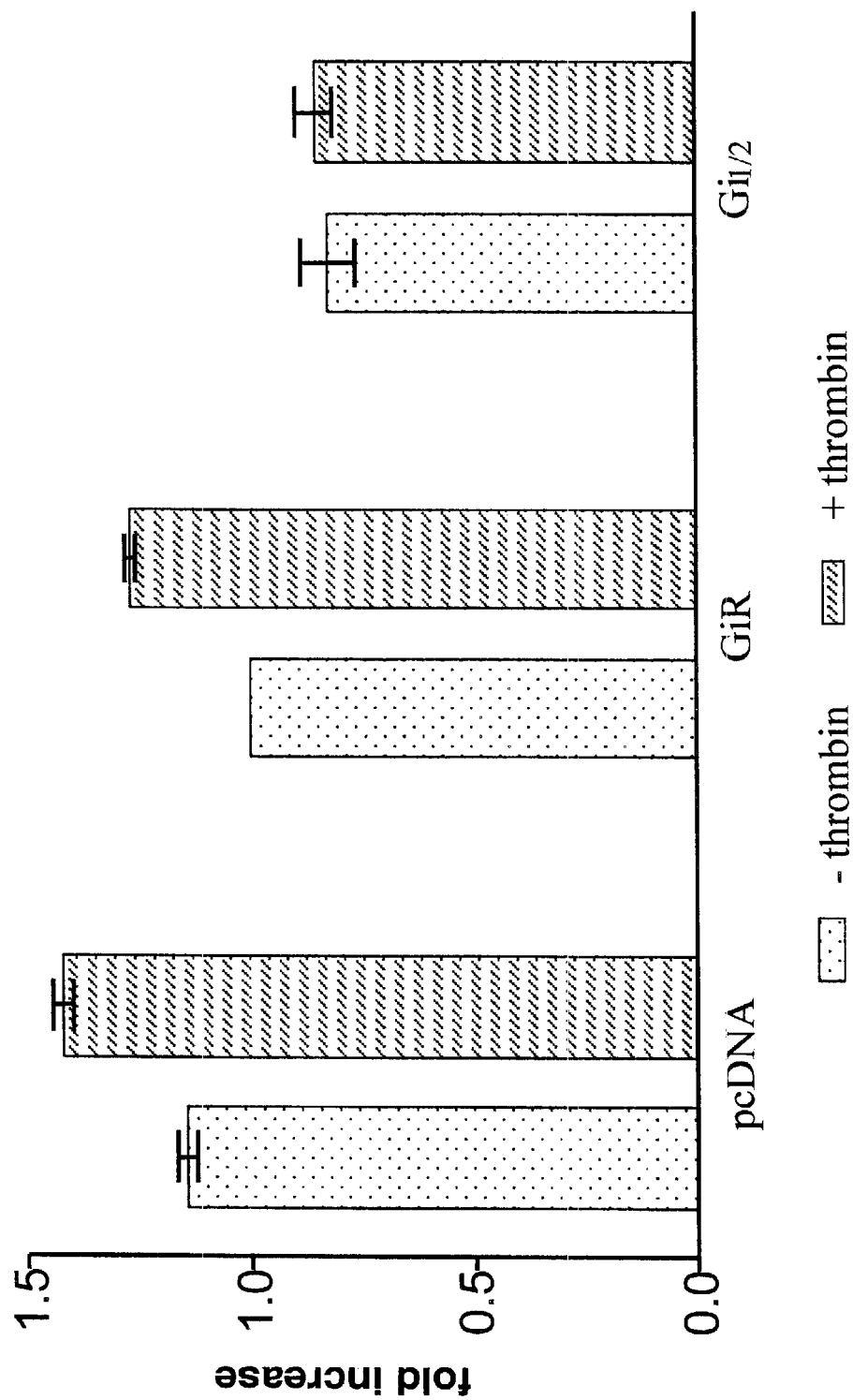
FIG. 6 is a graph which depicts a comparison of the thrombin-stimulated proliferative response of bovine pulmonary arterial endothelial (BPAE) cells transiently transfected with pcDNA 3.1, (pcDNA), pcDNA-Gα$_i$R (GiR), or pcDNA-Gα$_{i1/2}$ (Gi$_{1/2}$). The data represents at least three independent experiments, each done in duplicate.

Bovine pulmonary arterial endothelial (BPAE) cells were transfected with pcDNA3.1 (vector only), pcDNA-Gi, or pcDNA-GiR using electroporatoration and allowed to recover for 24 hours. Following recovery cells were plated in a 96 well plate at equal density. Cells were allowed to adhere for 3 hours, followed by stimulation with 100 nM thrombin or carrier alone for 18 hours. To measure proliferation, cells were labeled with 5-bromo-2 'deoxyuridine (BrdU) for 2hrs and then fixed and denatured using the Biotrak cell proliferation ELISA system (Amersham Pharmacia Biotech; London, UK). After blocking, cells were incubated with peroxidase-labelled anti-BrdU, washed 3× and incubated with substrate. The reaction was stopped with 1M sulphuric acid and the $OD_{450}$ was measured. Results shown in FIG. 6 provide data which has been normalized to a value of 1.0 for unstimulated cells transfected with pcDNA-GiR. Thrombin stimulated proliferation of endothelial cells is thought to be primarily through the Gi pathway. When the pcDNA-Gi$_{1/2}$ minigene was present, absolutely no thrombin-mediated increase in proliferation was observed.

c. Blockade of Thrombin-Stimulated PAR-1 Gene Induction

Thrombin treatment of cells induces the expression of the gene encoding its GPCR, PAR-1. This induction is mediated through the PAR-1 gene promotor sequence. The PAR-1 gene promotor sequence can be made to direct the expression of a reporter gene such as, the luciferase gene, thereby providing a means of observing the level of PAR-1 gene induction occurring in response to thrombin treatment of cells.

PAR-1 gene induction was demonstrated using a luciferase reporter assay as follows. A PAR-1 promoter sequence comprising 1.82 kilobases was inserted upstream of the gene, Firefly (*Photinus pyralis*) luciferase in a pGL2 vector DNA to generate the plasmid DNA, PCR-1/Luc. The sea pansy (*Renilla reniformis*) luciferase gene operably linked to the Herpes Simplex Virus-Thymidine Kinase promoter (TK) in a pRL vector DNA (TK/pRL) served as an internal control to correct for experimental variation. HMEC were co-transfected with 100 nanograms each of a reporter DNA, PCR-1/Luc or TK/pRL, and one of pcDNA3.1, pcDNA-G$\alpha_i$, or pcDNA-G$\alpha_i$R using protocols and reagents described in the previous Example. Twenty four hours post-transfection, HMEC were incubated in serum-free culture media (Dulbecco's Modified Eagles Medium, DMEM) for 2 hr at 37° C., following which, thrombin was added to the culture media at a concentration of 10 nanomolar. The cells were then incubated at 37° C. for four hours and lysed. For pertussis toxin pretreatment experiments, pertussis toxin was added to the cells in culture media at a concentration of 100 nanograms per milliliter, and the cells were incubated at 37° C. for at least 8 hours prior to treatment with thrombin. For the luciferase assay, a 20 microliter aliquot of the cell lysate was treated using protocols and reagents provided with the Dual Luciferase Reagent Assay System (Promega, Madison, Wis.).

Figure 7:
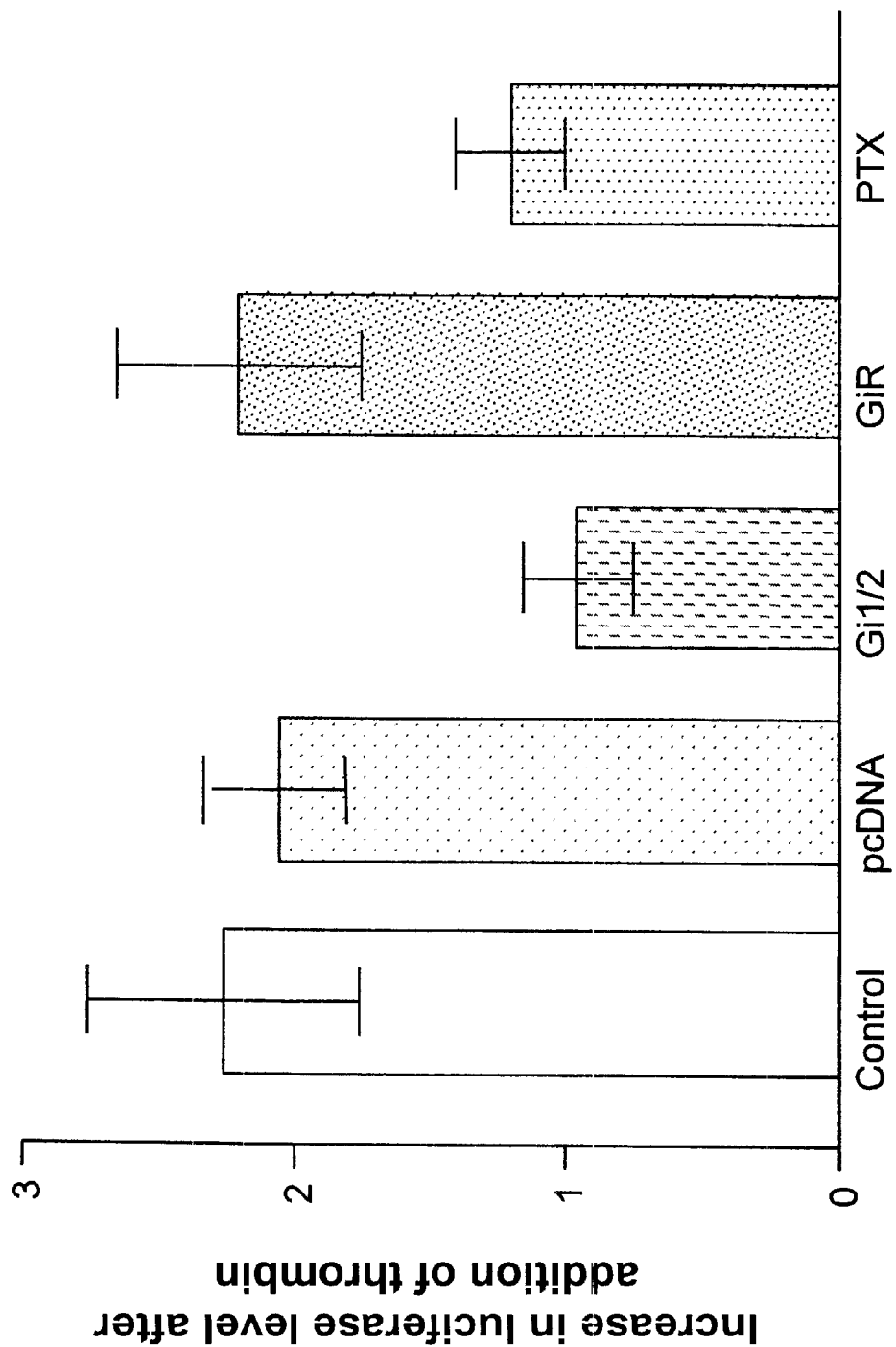
FIG. 7 is a graph which depicts a comparison of thrombin-stimulated luciferase acivity as a measure of PAR-1 gene expression in HMEC which are either treated with pertussis toxin or transiently transfected with pcDNA 3.1, (pcDNA3.1 (–)), pcDNA-Gα$_{i1/2}$ (Gi), or pcDNA-Gα$_i$R (Gi Random).

The results of the luciferase experiments are depicted in FIG. 7. The level of luciferase activity was higher after thrombin treatment in HMEC transiently transfected with any of the plasmids, PCR-1/Luc, pcDNA3.1, and pcDNA-G$\alpha_i$R as compared with the level luciferase activity in these cells in the absence of thrombin stimulation. In contrast, the level of luciferase activity did not increase in HMEC transfected with pcDNA-G$\alpha_i$. Pertussis toxin pretreatment of cells, which is known to block $G_i$ signaling also blocked the increase in luciferase levels. The results of these luciferase experiments demonstrate that the induction of PAR-1 gene expression, which is normally blocked by pertussis toxin, can also be blocked by transient transfection with a minigene DNA encoding the Gα carboxy terminal peptide. In addition, PAR-1 gene expression is not blocked by either of the control or random order minigene, pcDNA-Gα$_i$R.

d. Blockade of Thrombin-Stimulated Intracellular Ca$^{+2}$ Rise

HMEC were cotransfected with 1 microgram per well of a plasmid DNA encoding human πH3-CD8 and 1 microgram per well each of the control DNA, pcDNA 3.1, or pcDNA-Gα$_i$, pcDNA-Gα$_q$, or pcDNA-Gα$_i$R. Transfected cells were seeded on coverslips in a 24 well plate (i.e. 1 coverslip per well) at 48 hours post-transfection. Cells were incubated at 37° C. on the coverslips for 2 hours, following which approximately 2×10$^5$ microbeads adsorbed with the CD8 receptor protein were added to each well. The cells and microbeads were treated with a solution comprising 10 micromolar Oregon Green 488 BAPTA-1 and 0.1 % Pluronic F-127 (Molecular Probes, Eugene, Ore.), and incubated for 20–30 minutes at 37° C. Excess microbeads were removed by rinsing each well twice with a wash solution. Following the rinses, wash solution was added to each well, and the levels of intracellular Ca$^{2+}$ in each well were measured at ambient temperature. The fluorescence measurements of intracellular CA$^{2+}$ levels were made using an upright Olympus microscope (BX 50WI) equipped with Hamamatsu digital video camera and a Dell (Pentium II) computer enhanced with MetaMorph 3.5 software. Analysis of fluorescence intensity in the microscopic images was made using the NIH Image Program. To establish basal levels of intracellular Ca$^{2+}$, fluorescence intensity was recorded in cells 50 seconds prior to treatment of the cells with thrombin. Following thrombin treatment, fluorescence intensity was recorded in cells at 10 second intervals for a period of 1600 seconds.

Figure 8:
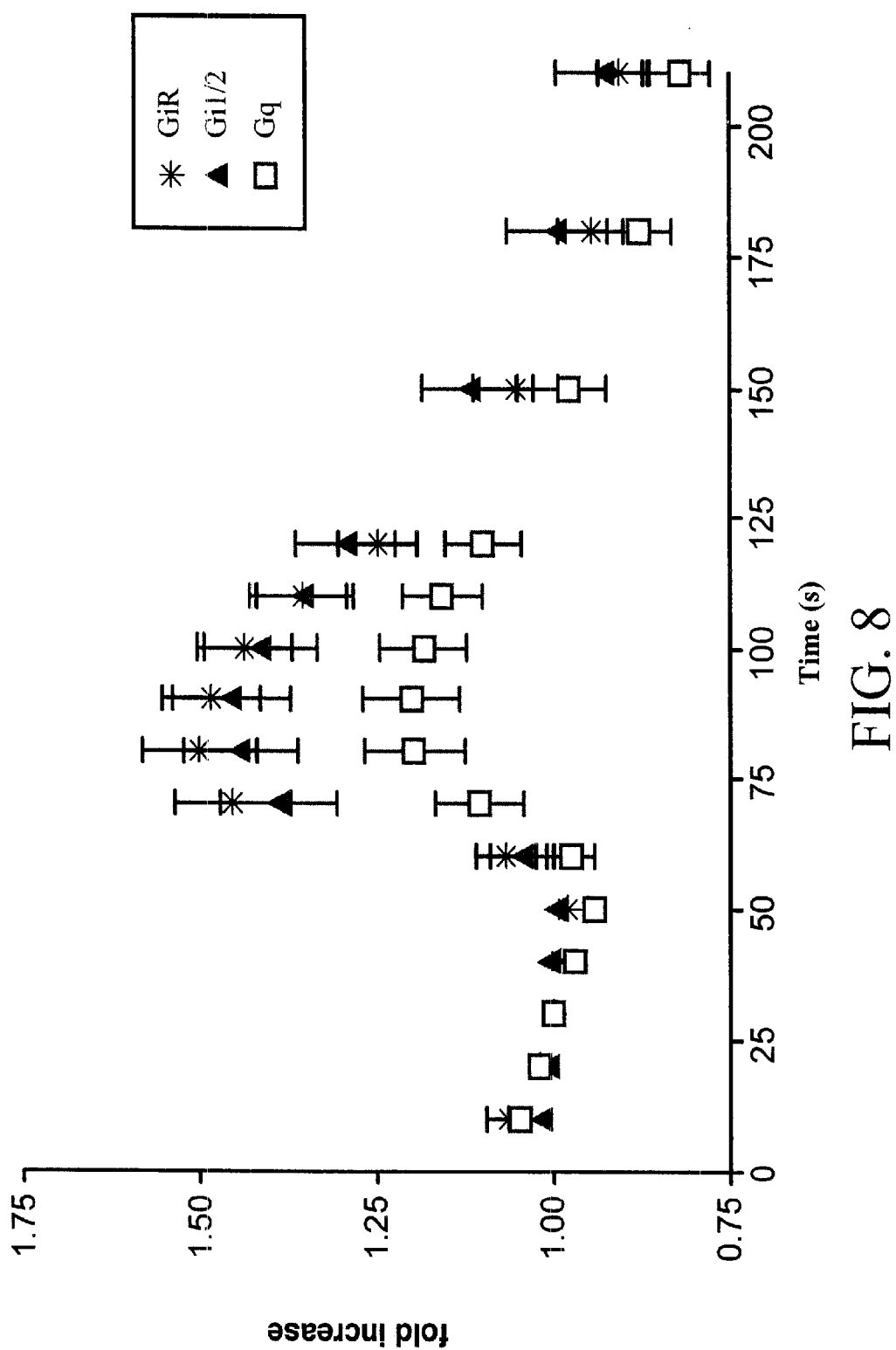
FIG. 8 is a graph which depicts a comparison of the level of thrombin-induced intracellular Ca$^{2+}$ rise in HMEC transiently transfected with pcDNA-Gα$_i$R(GiR), pcDNA-Gα$_{i1/2}$ (Gi1/2), or pcDNA-Gα$_q$ (Gq).

The tabular results of these experiments are depicted in FIG. 8. The the fluorescence intensities of recorded images are presented as a mean±standard error of the mean (SEM) for at least 15 individually recorded cells from each of the following transfection conditions, human πH3-CD8+the control DNA, pcDNA 3.1, human πH3-CD8+pcDNA-Gα$_i$, human πH3-CD8+pcDNA-Gα$_q$, and human πH3-CD8+pcDNA-Gα$_i$R.

The results of these experiments indicate that transfection of the minigene encoding the Gα$_q$ carboxy terminal peptide (pcDNA-Gα$_q$) blocks a rise in intracellular CA$^{2+}$ levels following thrombin stimulation. This is the expected result, since the rise in intracellular Ca$^{2+}$ levels is a downstream consequence of the interaction between PAR-1 and the G protein, G$_q$. Transient transfection of the other minigene DNAs, pcDNA-Gα$_i$, or pcDNA-Gα$_i$R, and the control DNA, pcDNA 3.1, do not block the rise in intracellular Ca$^{2+}$ levels. Thus these experiments demonstrate that the blockade of thrombin-induced rise in Ca$^{2+}$ by transfection of a minigene encoding the carboxy terminal peptide, Gα$_q$, is effective and is also specific for Gα$_q$.

e. Blockade of Thrombin-Stimulated Inositol Phosphate (IP) Accumulation

Thrombin is an agonist for the GPCR, PAR-1, which in-turn interacts with a G protein to initiate signaling events in a cell. Thrombin-induced IP accumulation is one downstream consequence of this interaction. Thus, blockade of an increase in response to thrombin treatment can be used to indicate the blockade of a G protein-mediated signaling event.

The increase in IP accumulation in HMEC in response to thrombin stimulation was carried out as follows. HMEC were seeded into 6-well plates at 1×10$^5$ cells per well. Cells were transiently transfected with 1 microgram per well of one of the minigene DNAs, pcDNA-Gα$_i$, and pcDNA-Gα$_q$, or the control DNA, pcDNA3.1. Cells were reseeded at 24 hours post-transfection onto 24-well plates, treated with tritium-labeled myoinositol having a specific radioactivity of 4 microcuries per milliliter ([$^3$H] myoinositol), and incubated for 24 hours at 37° C. Prior to stimulation 5 mM LicI was added to cells, and incubated for 1 hour. Stimulation was for 5 minutes with 1 nM human thrombin after which the medium was aspirated and cells lysed by addition of ice-cold methanol. Supernatant fractions were loaded onto AG1-8X Dowex columns and washed first with a solution comprising 40 millimolar ammonium formate to remove [$^3$H] inositol, and next, with a solution comprising 2 molar ammonium formate to elute [$^3$H] IP.

Figure 9:
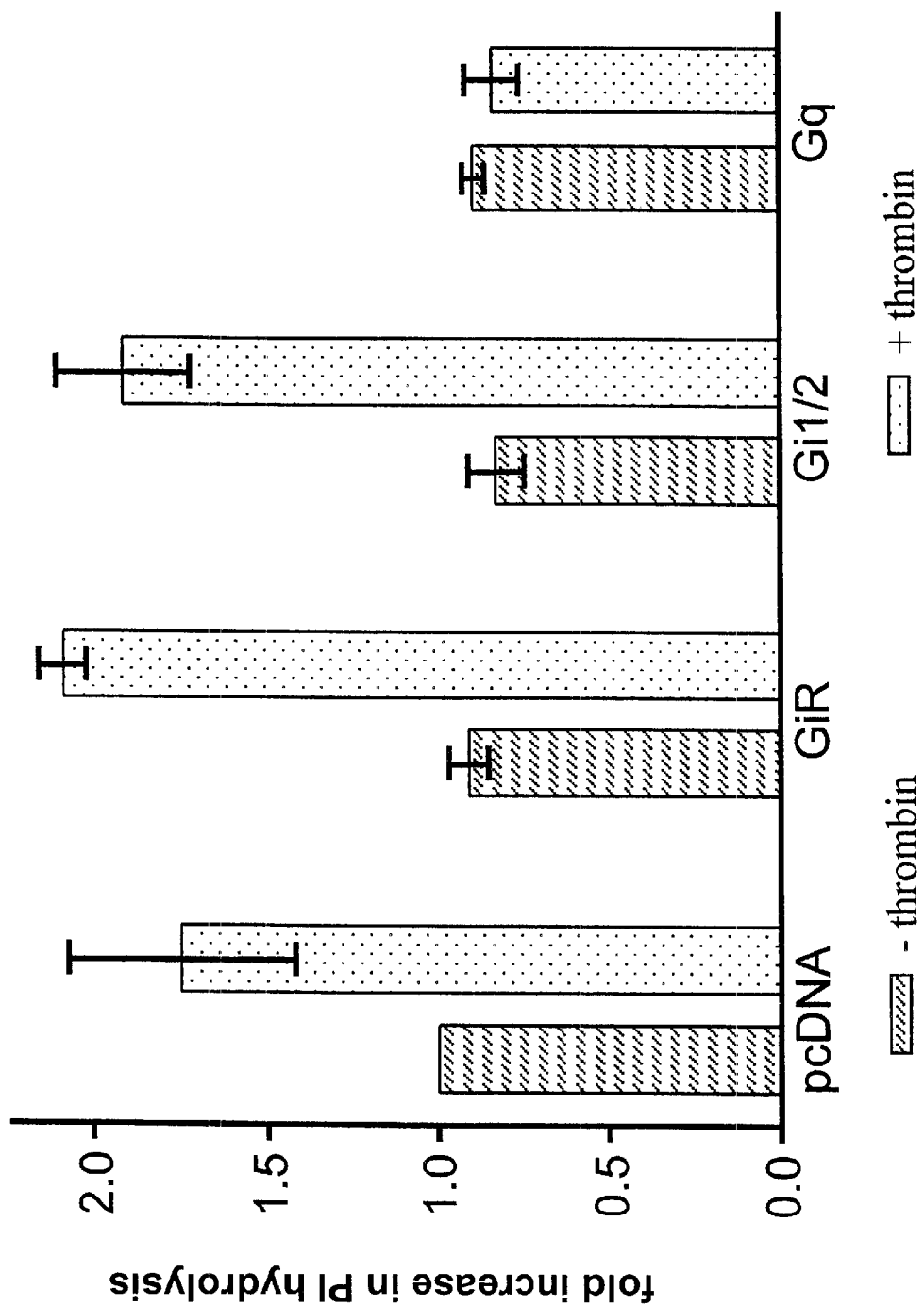
FIG. 9 is a graph which depicts a comparison of the level of inositol phosphate (IP) accumulation in HMEC transiently transfected with pcDNA 3.1, (pcDNA), pcDNA-Gα$_i$R (GiR), pcDNA-Gα$_{i1/2}$ (Gi1/2), or pcDNA-Gα$_q$ (Gq). The data represent at least three independent experiments performed in triplicate and expressed as a mean±standard error of the mean (SEM).

The results of IP accumulation experiments are depicted in FIG. 9. The data are expressed as a mean of two. independent experiments in which each DNA was transfected in triplicate (i.e. 1 micgrogram of a given DNA in each of three wells). The data for each experiment were generated using calculations performed as follows: counts per min [$^3$H]-IP fraction/counts per min [$^3$H]-inositol fraction+counts per min [$^3$H]-IP fraction.

The IP accumulation experiments demonstrate that transfection of the minigene encoding the Gα$_q$ carboxy terminal peptide (pcDNA-Gα$_q$) either alone or in combination with the minigene encoding the Gα$_i$ carboxy terminal peptide (pcDNA-Gα$_i$) blocks the accumulation of IP following thrombin stimulation. This is the expected result, since IP accumulation is a downstream consequence of the interaction between PAR-1 and the G protein, G$_q$. Transient transfection of pcDNA-Gα$_i$ by itself or the control DNA, pcDNA 3.1, do not block IP accumulation. Thus these experiments demonstrate that blockade of thrombin-induced IP accumulation by transfection of a minigene encoding the carboxy terminal peptide, Gα$_q$, is effective and specific for Gα$_q$.

f. Blockade of Thrombin-Induced Mitogen-activated Protein Kinase (MAPK) Activity HMEC were co-transfected with a plasmid DNA encoding hemagglutinin (HA-MAPK) and one of the plasmid DNAs, pcDNA3.1, pcDNA-Gα$_i$, pcDNA-Gα$_q$, or pcDNA-Gα$_i$R, in the manner described in the previous Examples. At 48 hours post-transfection, cells were transferred to serum-free medium and incubated for 2 hours at 37° C. For treatment with thrombin, cells were incubated at 37° C. for 5 minutes in a solution comprising 10 millimolar thrombin. Cells were lysed by treatment with RIPA. buffer according to the manufacturer's protocol. The resulting cell lysates were mixed with a solution comprising the 12CA5 antibody and preswollen Protein A-Sepharose, and subjected to immunoprecipitation using standard protocols. HA-MAPK activity was measured in the precipitated samples by incorporation of radioactive phosphorous ($^{32}$P) into myelin basic protein (MBP), i.e. phosphorylation of MBP by HA-MAPK in the presence of $^{32}$P-labeled adenosine triphosphate (ATP). Phosphorylation experiments were performed using standard protocols and reagents.

Figure 10:
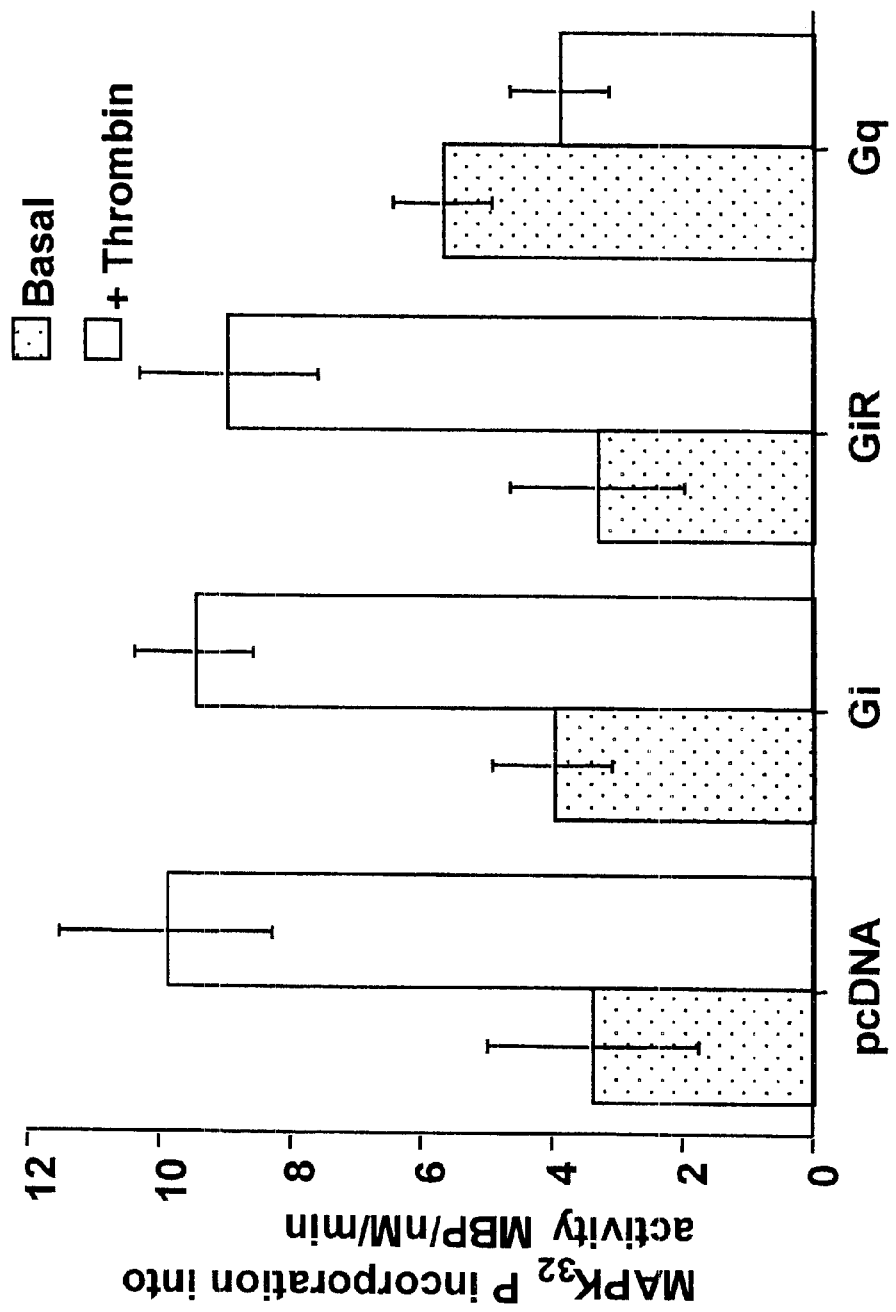
FIG. 10 is a graph which depicts a comparision of the level of thrombin-induced, mitogen-activated protein kinase (MAPK) activity in HMEC transiently transfected with selected minigenes.

The results of HA-MAPK activity experiments are depicted in FIG. 10. The data for HA-MAPK activity are presented as the $^{32}$P incorporation into MBP per nanomole of protein per minute of the phosphorylation reaction. Measurements of HA-MAPK activity were made with cell lysates from each of the following transfection conditions, HA-MAPK+the control DNA, pcDNA 3.1, HA-MAPK+pcDNA-Gα$_i$, HA-MAPK+pcDNA-Gα$_q$, and HA-MAPK+pcDNA-Gα$_i$R.

The results of these experiments indicate that transfection of the minigene encoding the Gα$_q$ carboxy terminal peptide (pcDNA-Gα$_q$) blocks the increase in MAPK activity levels following thrombin stimulation. This is the expected result, since MAPK activity is induced as a downstream consequence of the interaction between PAR-1 and the G protein, $G_q$. Transient transfection of the other minigene DNAs, pcDNA-$G\alpha_i$, or pcDNA-$G\alpha_s$R, and the control DNA, pcDNA 3.1, do not block the induction of MAPK activity by thrombin stimulation. Thus these experiments demonstrate an effective and specific blockade of a G protein-mediated by transfection of a minigene encoding the carboxy terminal peptide, $G\alpha_q$.

g. Inhibition of Thrombin-Mediated Stress Fiber Formation

Figure 11:
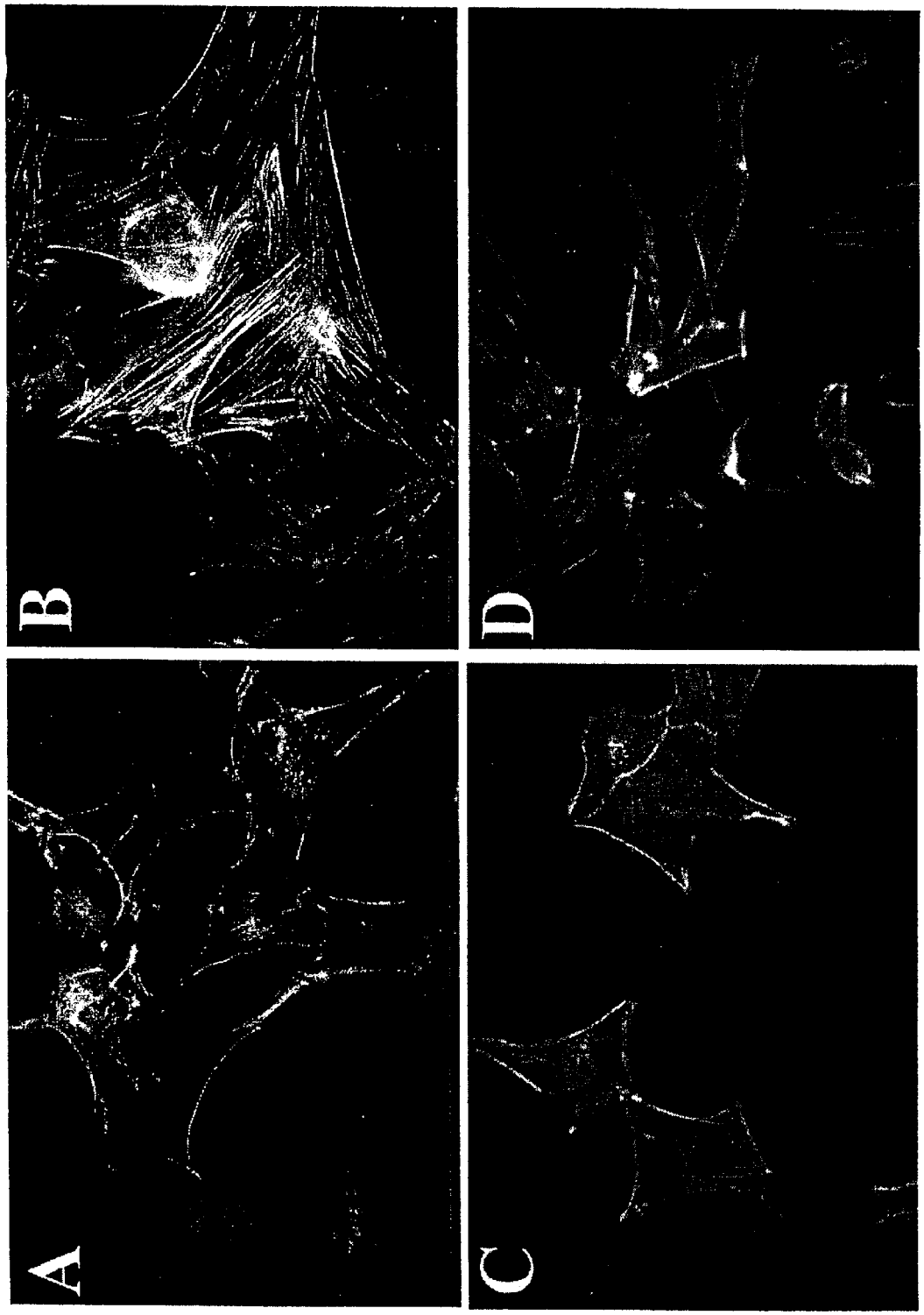
FIG. 11, comprising

HMEC were seeded on gelatin-coated coverslips, and transiently transfected with pcDNA (control), or the pcDNA-G12, or pcDNA-G13 minigenes in the presence of green fluorescent probe (GFP) expression vector (cDNAs ratio 5:1). Twenty-four hours later, cells were serum-starved for an additional 24 hours and then challenged with 10 nM thrombin for 5 min. Cells were washed with phosphate buffer saline (PBS), fixed with 4% paraformaldehyde, and permeabilized with 0.1% T riton X-100. Thereafter, cells were incubated for 30 min at room temperature with 1 $\mu$M rhodamine-phalloidin (Molecular Probes; Eugene, Ore.) to visualize polymerized F-actin. Cells were extensively washed, mounted using Vectashield antifade mounting medium (Vector Laboratories, Inc.; Burlingame, Calif.). Cells were observed with an inverted microscope (Diaphot 200, Nikon, Inc.; Melville, N.Y.) equipped for both differential interference contrast (DIC) microscopy and epifluorescence observation using a 60x oil-immersion objective. Fluorescence and DIC images were recorded for each cell field with a cooled, integrating CCD array camera (Imagepoint, Photometrix, Ltd.; Manchester, Conn.) connected to the microscope. In each coverslip, 100 GFP-expressing cells were analyzed. FIG. 11 shows that control cells which are transfected with the empty vector (pcDNA 3.1) and are serum starved and unstimulated have very few stress fibers (FIG. 11A; top left). Following stimulation with thrombin stress fibers are quickly induced (FIG. 11B; top right). However if cells are transfected with pcDNA-$G\alpha_{12}$ minigene (FIG. 11C; bottom left) or pcDNA-$G\alpha_{13}$ minigenes (FIG. 11D; bottom right) thrombin does not induce stress fiber formation.

h. Decrease in Thrombin-Induced Adhesion of HL-60 Cells

Figure 12:
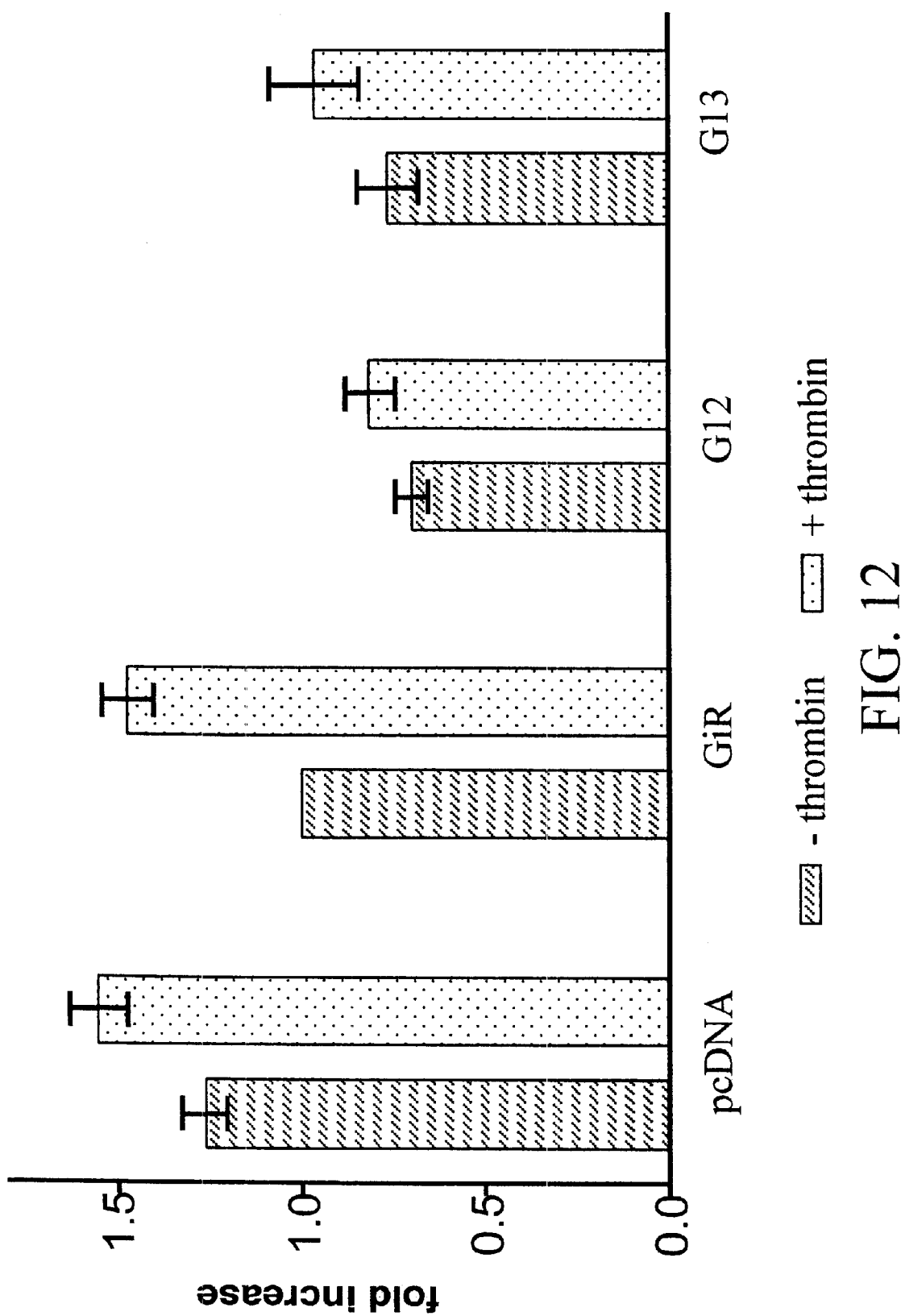
FIG. 12 is a graph depicting thrombin-induced adhesion of HL60 cells to HMEC transiently transfected with pcDNA 3.1, pcDNA-Gα$_i$R, pcDNA-Gα$_{12}$, or pcDNA-Gα$_{13}$.

HMEC cells were transfected in a 6 well plate using the Effectene Transfection Reagent (Qiagen; Carlsbad, Calif.) and pcDNA3.1, pcDNA3.1-GiR, pcDNA3.1-G12, or pcDNA3.1-G13. After 24 hrs cells were split into a 96 well to obtain $1\times10^4$ cells/well. Cells were allowed to adhere for 24 hrs, then stimulated with 1 nM thrombin for 1 hr. During this incubation period $1\times10^5$ HL60 cells were labeled with 5 $\mu$M calcein acetoxymethyl ester (calcein AM) (Molecular Probes; Eugene, Oreg.) for 30 min. Calcein AM labeled HL60 cells were washed twice and added in suspension to the transfected thrombin stimulated HMEC cells. After 1 hr at 37° C. nonadherent HL60 cells were removed by washing and 200 $\mu$l of PBS was added to each well. Fluorescence of the remaining calcein AM labeled HL60 cells was measured using a fluorescein filter with absorbance at 494 nm and emission at 517 nm. The results shown in FIG. 12 represent data that have been normalized to a value of 1.0 for unstimulated pcDNA-$G\alpha_i$R transfected cells. The presence of either the pcDNA-$G\alpha_{12}$ or pcDNA-$G\alpha_{13}$ minigene inhibits the normally observed thrombin-mediated increase in HL-60 cell adhesion to endothelial cells.

i. Blockade of Thrombin-Induced Transendothelial Electrical Resistance (TEER).

Endothelial cells undergo morphological changes in response to thrombin stimulation. Such changes coincide with other biochemical sequelae and with increased proliferation of the endothelial cells. One consequence of the shape change is decreased resistance of the cells to electrical current. Thus, a measure of the decrease in the resistance of endothelial cells to electrical current, i.e. transendothelial electrical resistance (TEER), can be used to measure the occurrence of a G protein-mediated signaling event responsible for the shape change.

The TEER of HMEC was measured as follows. HMEC were transiently transfected with 1 microgram per well of one of the minigene DNAs, pcDNA-$G\alpha_i$, and pcDNA-$G\alpha_s$, pcDNA-$G\alpha_i$R or the control DNA, pcDNA3.1. At 24 hours post-transfection, the cells were reseeded and grown in culture medium at 37° C. The resulting monolayers of cells were subjected to an alternating current of 50 microamperes by passing the current at 2 pulses per minute across each monolayer. Treatment with thrombin was carried out as described in the previous Examples.

Figure 14:
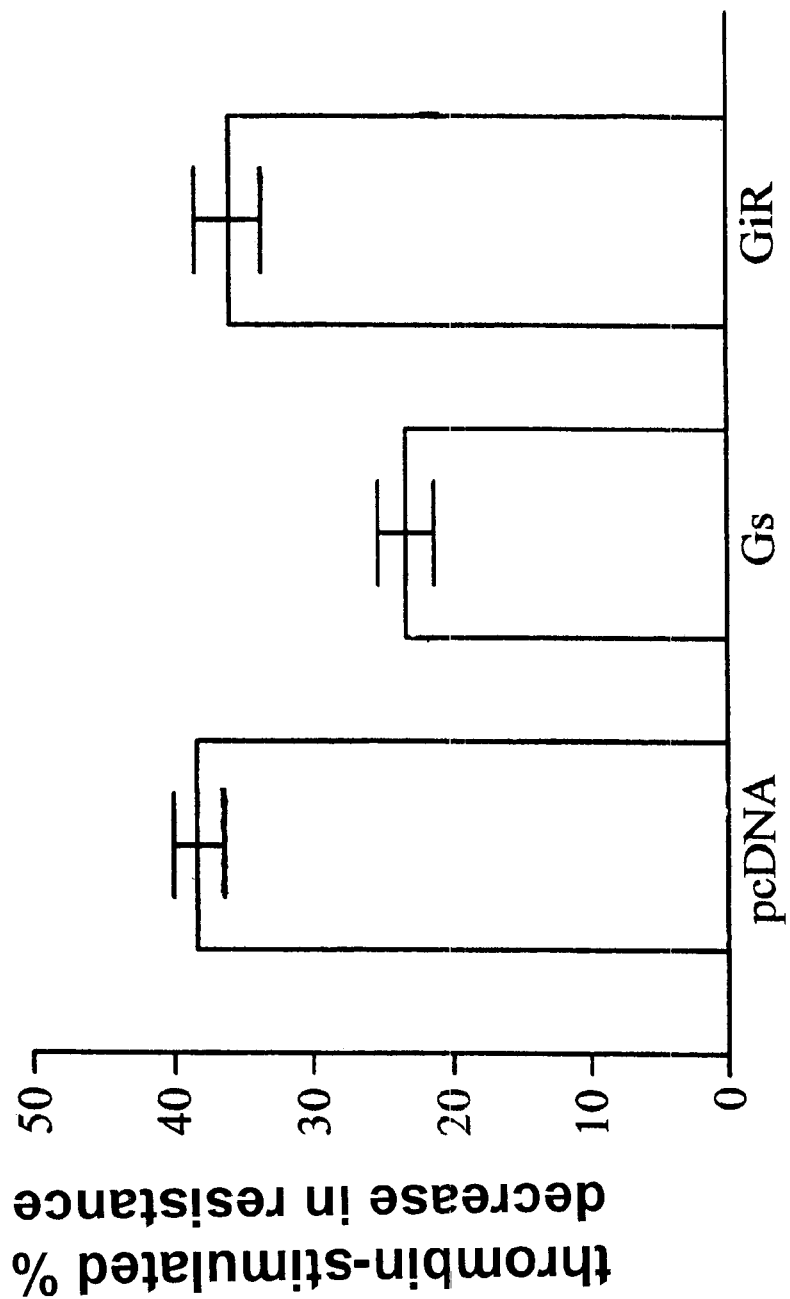
FIG. 14 is a graph which depicts a comparison of the relative levels of thrombin-induced transendothelial electrical resistance (TEER) in HMEC transiently transfected with selected minigenes.

The results of these experiments are depicted in FIG. 14. The basal level of TEER was decreased by 40% in HMEC transfected with pcDNA-$G\alpha_s$ minigene compared with the control DNA (pcDNA 3.1). Following thrombin stimulation, HMEC transfected with pcDNA 3.1 and pcDNA-$G\alpha_i$R, exhibited decreases in TEER of 36% and 39%, respectively. In contrast, HMEC transfected with pcDNA-$G\alpha_s$ exhibited a 23% decrease in TEER.

The results of the TEER experiments demonstrate that Gs mediates signaling events that ultimately result in endothelial cell shape changes, and that such pathways can be blocked effectively and specifically by the pcDNA-$G\alpha_s$ minigene.

The experiments described in the Examples presented herein demonstrate that minigenes encoding $G\alpha$ carboxy terminal peptides are useful for effectively and specifically targeting the $G\alpha$-GPCR interface and blocking G protein-mediated signaling events.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. An isolated nucleic acid comprising a minigene, wherein said in minigene encodes a carboxy terminal guanine nucleotide-binding protein alpha subunit (Gα) peptide, wherein said peptide blocks the site of binding between a G protein and a G protein coupled receptor in a cell, and further wherein the nucleotide sequence of said minigene consists of a nucleotide sequence selected from the group consisting of SEQ ID NOs: 2, 3, 4, 5, 6, 7, 8, 9, 10, 11, 12, 13, and 14.

2. The isolated nucleic acid of claim 1, wherein the amino acid sequence of said carboxy terminal guanine nucleotide-binding protein alpha subunit (Gα) peptide consists of an amino acid sequence selected from the group consisting of SEQ ID NOs: 15, 16, 17, 18, 19, 20, 21, 22, 23, 24, 25, 26, 27, 28, and 29.

3. The isolated nucleic acid of claim 1, further comprising at least one of a promoter and a ribosomal binding site.

4. The isolated nucleic acid of claim 3, further comprising a translation initiation codon and a translation termination codon.

5. The isolated nucleic acid of claim 1, wherein said cell is a human cell.

6. A composition comprising the isolated nucleic acid of claim 1 and a carrier.

7. A carboxy terminal Gα peptide wherein said peptide consists of an amino acid sequence selected from the group consisting of SEQ ID NOs: 15, 16, 17, 18, 19, 20, 21, 22, 23, 24, 25, 26, 27, 28, and 29.

8. A composition comprising a carboxy terminal guanine nucleotide-binding protein alpha subunit (Gα) peptide wherein said peptide consists of an amino acid sequence selected from the group consisting of SEQ ID NOs: 15, 16, 17, 18, 19, 20, 21, 22, 23, 24, 25, 26, 27, 28, and 29, and a carrier.

* * * * *

SEQUENCE LISTING

<160> NUMBER OF SEQ ID NOS: 47

<210> SEQ ID NO 1
<211> LENGTH: 57

```
<212> TYPE: DNA
<213> ORGANISM: Artificial Sequence
<220> FEATURE:
<223> OTHER INFORMATION: minigene

<400> SEQUENCE: 1
gatccgccgc caccatggaa atcaaggaaa acctgaagga ctgcggcctc ttctgaa        57

<210> SEQ ID NO 2
<211> LENGTH: 57
<212> TYPE: DNA
<213> ORGANISM: Artificial Sequence
<220> FEATURE:
<223> OTHER INFORMATION: minigene

<400> SEQUENCE: 2
gatccgccgc caccatggga atcaagaaca acctgaagga ctgcggcctc ttctgaa        57

<210> SEQ ID NO 3
<211> LENGTH: 57
<212> TYPE: DNA
<213> ORGANISM: Artificial Sequence
<220> FEATURE:
<223> OTHER INFORMATION: minigene

<400> SEQUENCE: 3
gatccgccgc caccatggga aacggcatca agtgcctctt caacgacaag ctgtgaa        57

<210> SEQ ID NO 4
<211> LENGTH: 57
<212> TYPE: DNA
<213> ORGANISM: Artificial Sequence
<220> FEATURE:
<223> OTHER INFORMATION: minigene

<400> SEQUENCE: 4
gatccgccgc caccatggga attaaaaaca acttaaagga atgtggactt tattgaa        57

<210> SEQ ID NO 5
<211> LENGTH: 57
<212> TYPE: DNA
<213> ORGANISM: Artificial Sequence
<220> FEATURE:
<223> OTHER INFORMATION: minigene

<400> SEQUENCE: 5
gatccgccgc caccatggga atcgccaaaa acctgcgggg ctgtggactc tactgaa        57

<210> SEQ ID NO 6
<211> LENGTH: 57
<212> TYPE: DNA
<213> ORGANISM: Artificial Sequence
<220> FEATURE:
<223> OTHER INFORMATION: minigene

<400> SEQUENCE: 6
gatccgccgc caccatggga attgccaaca acctccgggg ctgcggcttg tactgaa        57

<210> SEQ ID NO 7
<211> LENGTH: 57
<212> TYPE: DNA
<213> ORGANISM: Artificial Sequence
<220> FEATURE:
<223> OTHER INFORMATION: minigene

<400> SEQUENCE: 7
```
gatccgccgc caccatggga atacagaaca atctcaagta cattggcctt tgctgaa    57

<210> SEQ ID NO 8
<211> LENGTH: 57
<212> TYPE: DNA
<213> ORGANISM: Artificial Sequence
<220> FEATURE:
<223> OTHER INFORMATION: minigene

<400> SEQUENCE: 8
gatccgccgc caccatggga ctgcagctga acctgaagga gtacaatctg gtctgaa    57

<210> SEQ ID NO 9
<211> LENGTH: 57
<212> TYPE: DNA
<213> ORGANISM: Artificial Sequence
<220> FEATURE:
<223> OTHER INFORMATION: minigene

<400> SEQUENCE: 9
gatccgccgc caccatggga ctccagttga acctgaagga gtacaatgca gtctgaa    57

<210> SEQ ID NO 10
<211> LENGTH: 57
<212> TYPE: DNA
<213> ORGANISM: Artificial Sequence
<220> FEATURE:
<223> OTHER INFORMATION: minigene

<400> SEQUENCE: 10
gatccgccgc caccatggga cagcggatgc acctcaagca gtatgagctc ttgtgaa    57

<210> SEQ ID NO 11
<211> LENGTH: 57
<212> TYPE: DNA
<213> ORGANISM: Artificial Sequence
<220> FEATURE:
<223> OTHER INFORMATION: minigene

<400> SEQUENCE: 11
gatccgccgc caccatggga ctacagctaa acctaaggga attcaacctt gtctgaa    57

<210> SEQ ID NO 12
<211> LENGTH: 57
<212> TYPE: DNA
<213> ORGANISM: Artificial Sequence
<220> FEATURE:
<223> OTHER INFORMATION: minigene

<400> SEQUENCE: 12
gatccgccgc caccatggga ctcgcccggt acctggacga gattaatctg ctgtgaa    57

<210> SEQ ID NO 13
<211> LENGTH: 57
<212> TYPE: DNA
<213> ORGANISM: Artificial Sequence
<220> FEATURE:
<223> OTHER INFORMATION: minigene

<400> SEQUENCE: 13
gatccgccgc caccatggga ctgcaggaga acctgaagga catcatgctg cagtgaa    57

<210> SEQ ID NO 14
<211> LENGTH: 57
<212> TYPE: DNA
<213> ORGANISM: Artificial Sequence

```
<220> FEATURE:
<223> OTHER INFORMATION: minigene

<400> SEQUENCE: 14
gatccgccgc caccatggga cagcgcatgc accttcgtca gtacgagctg ctctgaa        57

<210> SEQ ID NO 15
<211> LENGTH: 13
<212> TYPE: PRT
<213> ORGANISM: Artificial Sequence
<220> FEATURE:
<223> OTHER INFORMATION: G alpha t peptide

<400> SEQUENCE: 15

Met Gly Ile Lys Glu Asn Leu Lys Asp Cys Gly Leu Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: G alpha i 1/2 peptide

<400> SEQUENCE: 16

Met Gly Ile Lys Asn Asn Leu Lys Asp Cys Gly Leu Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: G alpha i R peptide

<400> SEQUENCE: 17

Met Gly Asn Gly Ile Lys Cys Leu Phe Asn Asp Lys Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: G alpha i 3 peptide

<400> SEQUENCE: 18

Met Gly Ile Lys Asn Asn Leu Lys Glu Cys Gly Leu Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: G alpha o 2 peptide

<400> SEQUENCE: 19

Met Gly Ile Ala Lys Asn Leu Arg Gly Cys Gly Leu Tyr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: G alpha o 1 peptide
```

<400> SEQUENCE: 20

Met Gly Ile Ala Asn Asn Leu Arg Gly Cys Gly Leu Tyr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: G alpha z

<400> SEQUENCE: 21

Met Gly Ile Gln Asn Asn Leu Lys Tyr Ile Gly Leu Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: G alpha 11 peptide

<400> SEQUENCE: 22

Met Gly Leu Gln Leu Asn Leu Lys Glu Tyr Asn Leu Val
1               5                   10

<210> SEQ ID NO 23
<211> LENGTH: 13
<212> TYPE: PRT
<213> ORGANISM: Artificial Sequence
<220> FEATURE:
<223> OTHER INFORMATION: G alpha q peptide

<400> SEQUENCE: 23

Met Gly Leu Gln Leu Asn Leu Lys Glu Tyr Asn Ala Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: G alpha olf peptide

<400> SEQUENCE: 24

Met Gly Gln Arg Met His Leu Lys Gln Tyr Glu Leu Leu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: G alpha 14 peptide

<400> SEQUENCE: 25

Met Gly Leu Gln Leu Asn Leu Arg Glu Phe Asn Leu Val
1               5                   10

<210> SEQ ID NO 26
<211> LENGTH: 13
<212> TYPE: PRT
<213> ORGANISM: Artificial Sequence
<220> FEATURE:
<223> OTHER INFORMATION: G alpha 15/16 peptide -continued

```
<400> SEQUENCE: 26

Met Gly Leu Ala Arg Tyr Leu Asp Glu Ile Asn Leu Leu
1               5                   10

<210> SEQ ID NO 27
<211> LENGTH: 13
<212> TYPE: PRT
<213> ORGANISM: Artificial Sequence
<220> FEATURE:
<223> OTHER INFORMATION: G alpha 12 peptide

<400> SEQUENCE: 27

Met Gly Leu Gln Glu Asn Leu Lys Asp Ile Met Leu Gln
1               5                   10

<210> SEQ ID NO 28
<211> LENGTH: 13
<212> TYPE: PRT
<213> ORGANISM: Artificial Sequence
<220> FEATURE:
<223> OTHER INFORMATION: G alpha 13 peptide

<400> SEQUENCE: 28

Met Gly Leu His Asp Asn Leu Lys Gln Leu Met Leu Gln
1               5                   10

<210> SEQ ID NO 29
<211> LENGTH: 13
<212> TYPE: PRT
<213> ORGANISM: Artificial Sequence
<220> FEATURE:
<223> OTHER INFORMATION: G alpha s peptide

<400> SEQUENCE: 29

Met Gly Gln Arg Met His Leu Arg Gln Tyr Glu Leu Leu
1               5                   10

<210> SEQ ID NO 30
<211> LENGTH: 33
<212> TYPE: DNA
<213> ORGANISM: Homo sapiens

<400> SEQUENCE: 30
attaaaaaca acttaaagga atgtggactt tat                               33

<210> SEQ ID NO 31
<211> LENGTH: 33
<212> TYPE: DNA
<213> ORGANISM: Homo sapiens

<400> SEQUENCE: 31
atcgccaaaa acctgcgggg ctgtggactc tac                               33

<210> SEQ ID NO 32
<211> LENGTH: 33
<212> TYPE: DNA
<213> ORGANISM: Homo sapiens

<400> SEQUENCE: 32
atacagaaca atctcaagta cattggcctt tgc                               33

<210> SEQ ID NO 33
<211> LENGTH: 33
<212> TYPE: DNA
<213> ORGANISM: Homo sapiens
```

<400> SEQUENCE: 33
ctgcagctga acctgaagga gtacaatctg gtc					33

<210> SEQ ID NO 34
<211> LENGTH: 33
<212> TYPE: DNA
<213> ORGANISM: Homo sapiens

<400> SEQUENCE: 34
cagcggatgc acctcaagca gtatgagctc ttg					33

<210> SEQ ID NO 35
<211> LENGTH: 33
<212> TYPE: DNA
<213> ORGANISM: Homo sapiens

<400> SEQUENCE: 35
ctacagctaa acctaaggga attcaacctt gtc					33

<210> SEQ ID NO 36
<211> LENGTH: 33
<212> TYPE: DNA
<213> ORGANISM: Homo sapiens

<400> SEQUENCE: 36
ctcgcccggt acctggacga gattaatctg ctg					33

<210> SEQ ID NO 37
<211> LENGTH: 33
<212> TYPE: DNA
<213> ORGANISM: Homo sapiens

<400> SEQUENCE: 37
ctgcaggaga acctgaagga catcatgctg cag					33

<210> SEQ ID NO 38
<211> LENGTH: 33
<212> TYPE: DNA
<213> ORGANISM: Homo sapiens

<400> SEQUENCE: 38
ctgcatgaca acctcaagca gcttatgcta cag					33

<210> SEQ ID NO 39
<211> LENGTH: 11
<212> TYPE: PRT
<213> ORGANISM: Homo sapiens

<400> SEQUENCE: 39

Ile Lys Asn Asn Leu Lys Glu Cys Gly Leu Tyr
1               5                   10

<210> SEQ ID NO 40
<211> LENGTH: 11
<212> TYPE: PRT
<213> ORGANISM: Homo sapiens

<400> SEQUENCE: 40

Ile Ala Lys Asn Leu Arg Gly Cys Gly Leu Tyr
1               5                   10

<210> SEQ ID NO 41

```
<211> LENGTH: 11
<212> TYPE: PRT
<213> ORGANISM: Homo sapiens

<400> SEQUENCE: 41

Ile Gln Asn Asn Leu Lys Tyr Ile Gly Leu Cys
1               5                   10

<210> SEQ ID NO 42
<211> LENGTH: 11
<212> TYPE: PRT
<213> ORGANISM: Homo sapiens

<400> SEQUENCE: 42

Leu Gln Leu Asn Leu Lys Glu Tyr Asn Leu Val
1               5                   10

<210> SEQ ID NO 43
<211> LENGTH: 11
<212> TYPE: PRT
<213> ORGANISM: Homo sapiens

<400> SEQUENCE: 43

Gln Arg Met His Leu Lys Gln Tyr Glu Leu Leu
1               5                   10

<210> SEQ ID NO 44
<211> LENGTH: 11
<212> TYPE: PRT
<213> ORGANISM: Homo sapiens

<400> SEQUENCE: 44

Leu Gln Leu Asn Leu Arg Glu Phe Asn Leu Val
1               5                   10

<210> SEQ ID NO 45
<211> LENGTH: 11
<212> TYPE: PRT
<213> ORGANISM: Homo sapiens

<400> SEQUENCE: 45

Leu Ala Arg Tyr Leu Asp Glu Ile Asn Leu Leu
1               5                   10

<210> SEQ ID NO 46
<211> LENGTH: 11
<212> TYPE: PRT
<213> ORGANISM: Homo sapiens

<400> SEQUENCE: 46

Leu Gln Glu Asn Leu Lys Asp Ile Met Leu Gln
1               5                   10

<210> SEQ ID NO 47
<211> LENGTH: 11
<212> TYPE: PRT
<213> ORGANISM: Homo sapiens

<400> SEQUENCE: 47

Leu His Asp Asn Leu Lys Gln Leu Met Leu Gln
1               5                   10
```